US008653038B2

(12) United States Patent
Sugiyama

(10) Patent No.: US 8,653,038 B2
(45) Date of Patent: Feb. 18, 2014

(54) **HLA-A* 1101-RESTRICTED WT1 PEPTIDE AND PHARMACEUTICAL COMPOSITION COMPRISING THE SAME**

(75) Inventor: Haruo Sugiyama, Minoo (JP)

(73) Assignee: International Institute of Cancer Immunology, Inc., Osaka (JP)

(*) Notice: Subject to any disclaimer, the term of this patent is extended or adjusted under 35 U.S.C. 154(b) by 368 days.

(21) Appl. No.: 12/521,533

(22) PCT Filed: Dec. 14, 2007

(86) PCT No.: PCT/JP2007/074146
§ 371 (c)(1),
(2), (4) Date: Jun. 26, 2009

(87) PCT Pub. No.: WO2008/081701
PCT Pub. Date: Jul. 10, 2008

(65) Prior Publication Data
US 2011/0098233 A1    Apr. 28, 2011

(30) Foreign Application Priority Data
Dec. 28, 2006    (JP) .................... 2006-355356

(51) Int. Cl.
*A61K 38/08*    (2006.01)
*C07K 7/06*    (2006.01)
*C07K 7/08*    (2006.01)
*A61K 38/10*    (2006.01)

(52) U.S. Cl.
USPC ........ 514/21.6; 514/19.3; 514/21.4; 530/326; 530/328

(58) Field of Classification Search
None
See application file for complete search history.

(56) References Cited

U.S. PATENT DOCUMENTS

| | | | |
|---|---|---|---|
| 5,595,756 A * | 1/1997 | Bally et al. .................. 424/450 |
| 6,207,375 B1 * | 3/2001 | Subramaniam et al. ...... 435/6.16 |
| 7,115,272 B1 | 10/2006 | Galger et al. |
| 7,144,581 B2 | 12/2006 | Galger |
| 7,622,119 B2 * | 11/2009 | Sugiyama .................. 424/185.1 |
| 2003/0039635 A1 | 2/2003 | Galger et al. |
| 2003/0072767 A1 | 4/2003 | Galger et al. |
| 2003/0082194 A1 | 5/2003 | Galger et al. |
| 2003/0082196 A1 * | 5/2003 | Gaiger et al. ............... 424/185.1 |
| 2003/0095971 A1 | 5/2003 | Galger et al. |
| 2003/0198622 A1 * | 10/2003 | Gaiger et al. ................ 424/93.2 |
| 2003/0235557 A1 | 12/2003 | Galger et al. |
| 2004/0018204 A1 | 1/2004 | Gaiger et al. |
| 2004/0126362 A1 | 7/2004 | Gaiger et al. |
| 2006/0121046 A1 * | 6/2006 | Gaiger et al. ............... 424/184.1 |
| 2006/0217297 A1 * | 9/2006 | Sugiyama et al. .............. 514/12 |
| 2007/0026008 A1 | 2/2007 | Galger et al. |
| 2007/0082860 A1 | 4/2007 | Sugiyama et al. |
| 2008/0152631 A1 | 6/2008 | Sugiyama |

FOREIGN PATENT DOCUMENTS

| | | |
|---|---|---|
| CN | 1756763 A | 4/2006 |
| EP | 1584627 A1 | 10/2005 |
| JP | 2006-45287 | 2/2006 |
| JP | 2006-280324 | 10/2006 |
| JP | 2008-069172 A | 3/2008 |
| WO | WO 94/23030 A2 | 10/1994 |
| WO | WO 00/18795 | 4/2000 |
| WO | wo 01/25273 a2 * | 4/2001 |
| WO | WO 01/25273 A3 | 4/2001 |
| WO | WO 01/62920 A2 | 8/2001 |
| WO | WO 02/28414 A1 | 4/2002 |
| WO | WO 03/037060 A2 | 5/2003 |
| WO | WO03/105855 | 12/2003 |
| WO | WO 03/106491 A2 | 12/2003 |
| WO | WO 03/106682 A1 | 12/2003 |
| WO | WO 2005/095598 A1 | 10/2005 |

OTHER PUBLICATIONS

Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Druckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Sporn MB, Suh N, "Chemoprevention of cancer," Carcinogenesis, 2000, 21(3): 525-530.*
Auerbach R, Akhtar N, Lewis RL, Shinners, BL, "Angiogenesis assays: Problems and pitfalls," Cancer and Metastais Reviews, 2000, 19: 167-172.*

(Continued)

*Primary Examiner* — Julie Ha
(74) *Attorney, Agent, or Firm* — Finnegan, Henderson, Farabow, Garrett & Dunner, LLP

(57) ABSTRACT

An HLA-A*1101-restricted WT1 peptide, specifically, a peptide comprising an amino acid sequence consisting of 9 contiguous amino acids from a WT1 protein, wherein the peptide has an ability to bind to an HLA-A*1101 molecule, and has an ability to induce a CTL is described. A peptide dimer having an ability to bind to an HLA-A*1101 molecule and having an ability to induce a CTL, in which two peptide monomers each comprising an amino acid sequence consting of 9 contiguous amino acids from a WT1 protein and comprising at least one cysteine residue are bound to each other through a disulfide bond is also described. Furthermore, a polynucleotide encoding the peptide, a pharmaceutical composition for the treatment and/or prevention of a cancer comprising the same and the like are provided.

11 Claims, 14 Drawing Sheets

(56) References Cited

OTHER PUBLICATIONS

Gura T, "Systems for Identifying New Drugs Are Often Faulty," Science, 1997, 278: 1041-1042.*
Jain RK, "Barriers to Drug Delivery in Solid Tumors," Scientific American, 1994, 58-65.*
Cancer Drug Design and Discovery Neidle, Stephen, ed. (Elsevier/Academic Press, 2008) pp. 427-431.*
Supplementary European Search Report (PCT/JP2007074146) dated Feb. 17, 2010.
A. Van Driessche et al., Antigen-specific cellular immunotherapy of leukemia, Leukemia, vol. 19, No. 11, Nov. 2005, pp. 1863-1871 XP-002565480.
Office Action dated Oct. 21, 2010 issued in corresponding Chinese application No. 200780048749.1.
Database UniProt [Online], May 1, 2000, SubName: Full=Wilm's tumor protein 1; XP002626118, retrieved from EBI accession No. UNIPROT:Q9TSS7.
Examination Report dated May 5, 2011 issued in corresponding New Zealand application.
Partial European Search Report dated May 18, 2011.
Office Action dated Mar. 30, 2011 Issued in corresponding Chinese application No. 200780048749.1.
English summary of Office Action issued in corresponding Israeli Application No. 199052.
Database UniProt [Online] May 1, 2000, "SubName: Full=Wilm's tumor protein 1; Flags: Fragment," XP002626118, retrieved from EBI accession No. UNIPROT:Q9TSS7 Database accession No. Q9TSS7.
European Search Report dated Aug. 8, 2011 issued in European Patent Application No. 10191234.3.
Examination Report dated Sep. 20, 2011 issued in corresponding New Zealand Application No. 577443.
Examination Report dated Sep. 20, 2011 issued in corresponding New Zealand Application No. 592509.
Examination Report dated Sep. 20, 2011 issued in corresponding New Zealand Application No. 592510.
Russian Office Action dated Jul. 22, 2011.
Daniel A. Haber et al., "An Internal Deletion within an 11p13 Zinc Finger Gene Contributes to the Development of Wilms' Tumor," Cell, 1990, vol. 61, pp. 1257-1269.
Katherine M. Call et al., "Isolation and Characterization of a Zinc Finger Polypeptide Gene at the Human Chromosome 11 Wilms' Tumor Locus," Cell, 1990, vol. 60, pp. 509-520.
A. L. Menke et al., "The Wilms' Tumor 1 Gene: Oncogene or Tumor Suppressor Gene?," International Review of Cytology, vol. 181, pp. 151-212.
Tamotsu Yamagami et al., "Growth Inhibition of Human Leukemic Cells by WT1 (Wilms tumor Gene) Antesense Oligodeoxynucleotides: Implications for the Involvement of WT1 in Leukemogenesis," Blood, 1996, vol. 87, No. 7, pp. 2878-2884.
Kazushi Inoue et al., "Wilms' Tumor Gene (TW1) Competes With Differentiation-Inducing Signal in Hematopoietic Progenitor Cells," Blood, 1998, vol. 91, No. 8, pp. 2969-2976.
Akihiro Tsuboi et al., "Constitutive expression of the Wilms' tumor gene WT1 inhibits the differentiation of myeloid progenitor cells but promotes their proliferation in response to granulocte-colony stimulating factor (G-CSF)," Leukemia Research, 1999, vol. 23, pp. 499-505.
Yoshihiro Oka et al., "Cancer Immunotherapy Targeting Wilms' Tumor Gene WT1 Product, "The Journal of Immunology, 2000, vol. 164, pp. 1873-1880.
Cornelis J. M. Melief et al., "T-Cell Immunotherapy of Tumors by Adoptive Transfer of Cytotoxic T Lymphocytes and by Vaccination with Minimal Essential Epitopes," Immunological Review, 1995, No. 146 pp. 167-177.
Jerome Ritz, "Tumor Immunity: Will New Keys Unlock the Door?," Journal of Clinical Oncology, vol. 12, No. 2, pp. 237-238.
Akihiro Tsuboi et al., "Cytotoxic T-Lymphocyte Response Elicited to Wilms' Tumor Gene WT1 Product by DNA Vaccination," Journal of Clinical Immunology, vol. 20, No. 3, 2000, pp. 195-202.
Yoshihiro Oka et al., "Human cytotoxic T-lymphocyte responses specific for peptides of the wild-type Wilms' tumor gene (WT1) product," Immunogenetics, 2000, vol. 51, pp. 99-107.
Hideki Ohminami et al. "HLA class I-restricted lysis of leukemia cells by a CD8+ cytotoxic T-lymphocyte clone specific for WT1 peptide," Blood, 2000, vol. 95, No. 1, pp. 285-293.
Liquan Gao et al., "Selective elimination of leukemic CD34+ progenitor cells by cytotoxic T lumphocytes specific for WT1," Blood, 2000, vol. 95, No. 7, pp. 2198-2203.
Examination Report dated Dec. 11, 2012, issued in Australian Patent Application No. 2007340679.
Office Action dated Dec. 31, 2012, issued in Malaysian Patent Application No. PI 20092279.
Correspondence dated Feb. 21, 2013, forwarding and describing an Office Action issued in Colombian Patent Application No. 09078403.
Guo et al., "Direct Recognition and Lysis of Leukemia Cells by WT1-Specific CD4+ T Lymphocytes in an HLA Class II-Restricted Manner," Blood, 106:1415-1418 (2005).
Office Action dated Feb. 26, 2013, issued in Japanese Patent Application No. 2008-552080.
Office Action dated Jul. 10, 2012, issued in corresponding Australian Patent Application No. 2007340679.
Office Action dated Aug. 3, 2012, issued in Chinese Patent Application No. 201110235501.4.
Correspondence dated Oct. 1, 2012, forwarding and describing Colombian Office Action issued in Colombian Patent Application 09078403.
Office Action dated Aug. 21, 2012, issued in Japanese Patent Application No. 2008-552080.
Examination Report dated May 4, 2011, issued in New Zealand Patent Application No. 592510.
Correspondence forwarding and describing Office Action issued in corresponding Mexican Patent Application No. MX/a/2009/007008, dated Jan. 17, 2012 (8 pages).
International Search Report issued in corresponding International Patent Application No. PCT/JP2007/074146, mailed Mar. 18, 2008.
International Preliminary Report on Patentability issued in corresponding International Patent Application No. PCT/JP2007/074146, dated Jun. 30, 2009.
Office Action dated Apr. 16, 2012, issued in corresponding Russian Patent Application No. 2009128979.
Correspondence forwarding and describing Office Action dated Apr. 16, 2012, issued in corresponding Israeli Patent Application No. 199,052.
Correspondence forwarding and describing Office Action dated Apr. 17, 2012, issued in corresponding Israeli Patent Application No. 215,332.
Correspondence forwarding and describing Office Action dated Apr. 17, 2012, issued in corresponding Israeli Patent Application No. 215,333.
Correspondence forwarding and describing Office Action dated Apr. 18, 2012, issued in corresponding Israeli Patent Application No. 215,334.
Extended European Search Report mailed May 29, 2012, in corresponding European Patent Application No. EP 12164856.2.
Extended European Search Report mailed May 29, 2012, in corresponding European Patent Application No. EP 12164855.4.
Office Action dated Jun. 7, 2012, issued in corresponding Ukrainian Patent Application No. 200907944.
Examination Report dated Jul. 16, 2012, issued in New Zealand Patent Application No. 592509.
Examination Report dated Jul. 16, 2012, issued in New Zealand Patent Application No. 592510.
Office Action dated Sep. 5, 2012, issued in Chinese Patent Application No. 201110235503.3.
Examination Report dated Jan. 9, 2012 issued in corresponding New Zealand Application No. 592509.
Examination Report dated Jan. 9, 2012 issued in corresponding New Zealand Application No. 592510.
Office Action dated Mar. 26, 2013, issued in Chinese Patent Application No. 201110235527.9.
Office Action dated Jun. 3, 2013, issued in Australian Patent Application No. 2007340679.

(56) References Cited

OTHER PUBLICATIONS

Database: GenBank: AAY18327.1 dated Feb. 24, 2006.
Database: GenBank: AAC60039.1 dated Nov. 8, 1996.
Database: GenBank: AAU78269.1 dated Sep. 22, 2004.
Database: GenBank: ABA65760.1 dated Oct. 7, 2005.
Database: GenBank: AAP01095.1 dated Apr. 10, 2003.
Office Action dated Jul. 5, 2013, issued in Colombian Patent Application No. 09078403.
Office Action received Sep. 11, 2013, issued in Egyptian Patent Application No. PCT 1007/2009.
Office Action dated Dec. 18, 2013, issued in Chinese Patent Application No. 201110235527.9.

* cited by examiner

Fig. 11
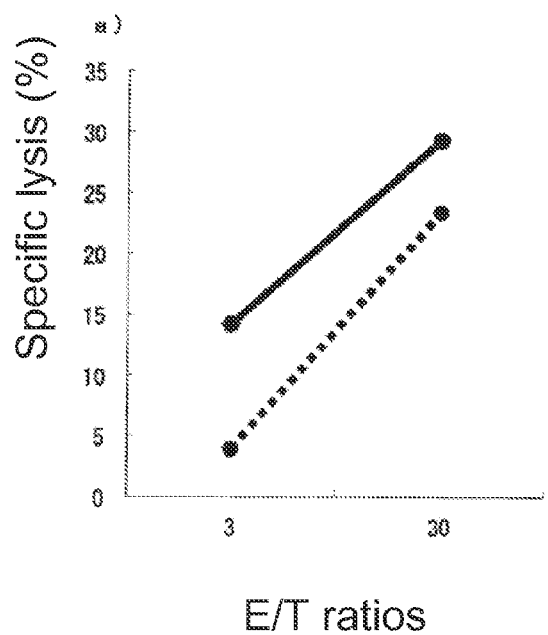
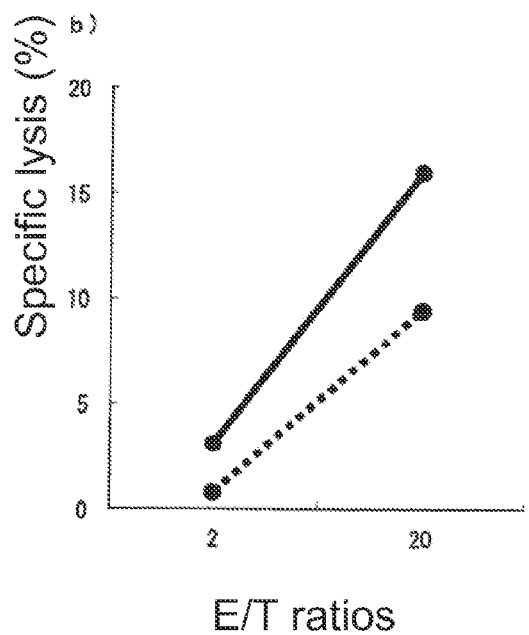

```
                         SEQUENCE LISTING

<160> NUMBER OF SEQ ID NOS: 13

<210> SEQ ID NO 1
<211> LENGTH: 449
<212> TYPE: PRT
<213> ORGANISM: Homo sapiens

<400> SEQUENCE: 1

Met Gly Ser Asp Val Arg Asp Leu Asn Ala Leu Leu Pro Ala Val Pro
 1               5                  10                  15

Ser Leu Gly Gly Gly Gly Gly Cys Ala Leu Pro Val Ser Gly Ala Ala
            20                  25                  30

Gln Trp Ala Pro Val Leu Asp Phe Ala Pro Pro Gly Ala Ser Ala Tyr
        35                  40                  45

Gly Ser Leu Gly Gly Pro Ala Pro Pro Ala Pro Pro Pro Pro
    50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
    130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
        195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270
```

-continued

```
Ser Asp Asn His Thr Thr Pro Ile Leu Cys Gly Ala Gln Tyr Arg Ile
        275                 280                 285

His Thr His Gly Val Phe Arg Gly Ile Gln Asp Val Arg Val Pro
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
        435                 440                 445

Leu

<210> SEQ ID NO 2
<211> LENGTH: 9
<212> TYPE: PRT
<213> ORGANISM: Homo sapiens

<400> SEQUENCE: 2

Ala Ala Gly Ser Ser Ser Ser Val Lys
 1               5

<210> SEQ ID NO 3
<211> LENGTH: 9
<212> TYPE: PRT
<213> ORGANISM: Homo sapiens

<400> SEQUENCE: 3

Pro Ile Leu Cys Gly Ala Gln Tyr Arg
 1               5

<210> SEQ ID NO 4
<211> LENGTH: 9
<212> TYPE: PRT
<213> ORGANISM: Homo sapiens

<400> SEQUENCE: 4

Arg Ser Ala Ser Glu Thr Ser Glu Lys
 1               5

<210> SEQ ID NO 5
<211> LENGTH: 9
<212> TYPE: PRT
<213> ORGANISM: Homo sapiens

<400> SEQUENCE: 5

Ser Ala Ser Glu Thr Ser Glu Lys Arg
 1               5
```

```
<210> SEQ ID NO 6
<211> LENGTH: 9
<212> TYPE: PRT
<213> ORGANISM: Homo sapiens

<400> SEQUENCE: 6

Ser His Leu Gln Met His Ser Arg Lys
 1               5

<210> SEQ ID NO 7
<211> LENGTH: 9
<212> TYPE: PRT
<213> ORGANISM: Homo sapiens

<400> SEQUENCE: 7

Thr Gly Val Lys Pro Phe Gln Cys Lys
 1               5

<210> SEQ ID NO 8
<211> LENGTH: 9
<212> TYPE: PRT
<213> ORGANISM: Homo sapiens

<400> SEQUENCE: 8

Lys Thr Cys Gln Arg Lys Phe Ser Arg
 1               5

<210> SEQ ID NO 9
<211> LENGTH: 9
<212> TYPE: PRT
<213> ORGANISM: Homo sapiens

<400> SEQUENCE: 9

Ser Cys Arg Trp Pro Ser Cys Gln Lys
 1               5

<210> SEQ ID NO 10
<211> LENGTH: 9
<212> TYPE: PRT
<213> ORGANISM: Homo sapiens

<400> SEQUENCE: 10

Asn Met His Gln Arg Asn Met Thr Lys
 1               5

<210> SEQ ID NO 11
<211> LENGTH: 9
<212> TYPE: PRT
<213> ORGANISM: Artificial Sequence
<220> FEATURE:
<223> OTHER INFORMATION: Modified WT1 peptide

<400> SEQUENCE: 11

Thr Ile Val Lys Pro Phe Gln Cys Lys
 1               5

<210> SEQ ID NO 12
<211> LENGTH: 9
<212> TYPE: PRT
<213> ORGANISM: Artificial Sequence
<220> FEATURE:
<223> OTHER INFORMATION: Modified WT1 peptide

<400> SEQUENCE: 12

Thr Val Val Lys Pro Phe Gln Cys Lys
 1               5
```

```
<210> SEQ ID NO 13
<211> LENGTH: 9
<212> TYPE: PRT
<213> ORGANISM: Homo sapiens

<400> SEQUENCE: 13

Gly Val Lys Pro Phe Gln Cys Lys Thr
 1               5
```

HLA-A*1101-RESTRICTED WT1 PEPTIDE AND PHARMACEUTICAL COMPOSITION COMPRISING THE SAME

TECHNICAL FIELD

The present invention relates to an HLA-A*1101-restricted WT1 peptide, specifically, a peptide comprising an amino acid sequence consisting of 9 contiguous amino acids from a WT1 protein, wherein the peptide has an ability to bind to an HLA-A*1101 molecule, and has an ability to induce a CTL. The present invention also relates to a peptide dimer having an ability to bind to an HLA-A*1101 molecule, and having an ability to induce a CTL, wherein two peptide monomers each comprising an amino acid sequence consisting of 9 contiguous amino acids from a WT1 protein and comprising at least one cysteine residue are bound to each other through a disulfide bond. Furthermore, the present invention relates to a polynucleotide encoding the peptide, a pharmaceutical composition for the treatment and/or prevention of a cancer comprising the same and the like.

BACKGROUND

WT1 gene (Wilms' tumor 1 gene) was identified as a gene responsible for Wilms tumor which is a renal cancer in children (Non-patent Documents 1 and 2). WT1 is a transcription factor having a zinc finger structure. At the beginning, the WT1 gene was considered to be a tumor suppressor gene. However, subsequent studies (Non-patent Documents 3, 4, 5 and 6) showed that the WT1 gene rather functions as an oncogene in hematopoietic tumors and solid cancers.

The WT1 gene is expressed at high levels in many types of malignant tumors. Then, it has been examined whether or not the WT1 gene product free of mutations, which is an autologous protein, has immunogenicity in a living body. The results revealed that the protein derived from the WT1 gene which is expressed at high levels in tumor cells is fragmented through intracellular processing, the resulting peptides form complexes with MHC class I molecules, and the complexes are presented on the surfaces of cells, and that CTLs recognizing such complexes can be induced by peptide vaccination (Non-patent Documents 7, 8 and 9). It was also shown that in a mouse immunized with a WT1 peptide or a WT1 cDNA, transplanted tumor cells expressing a WT1 gene are rejected with a high probability (Non-patent Documents 7 and 10), while normal tissues expressing physiologically the WT1 gene are not damaged by the induced CTLs (Non-patent Document 7). It was shown in in vitro experiments using human cells that when Db126 peptide or WH187 peptide (amino acids 187-195 of SEQ ID No: 1, SLGEQQYSV) having a high ability to bind to an HLA-A*0201 molecule, which is one of human MHC class I molecules, is used to stimulate human peripheral blood mononuclear cells having HLA-A*0201, WT1-specific CTLs are induced, the induced CTLs have a cytotoxic activity specific for tumor cells expressing endogenously a WT1 gene at high levels, and the cytotoxic activity of such CTLs is HLA-A2-restricted (Non-patent Document 11). It was shown in in vitro experiments in human cells using WT1 peptide that matches HLA-A*2402 (which is found most frequently in Japanese people among HLA-A alleles) (WT1235; amino acids 235-243 of SEQ ID No: 1, CMTWNQMNL) that WT1-specific CTLs (TAK-1) are induced (Non-patent Document 12), and the induced CTLs do not suppress the colony-forming activity of normal hematopoietic stem cells which partially express physiologically a WT1 gene (Non-patent Documents 12 and 13). These reports strongly suggest that not only in mice but also in human beings, WT1-specific CTLs can be induced, such CTLs have a cytotoxic activity against tumor cells expressing a WT1 gene at high levels, but do not have a cytotoxic activity against normal cells expressing physiologically a WT1 gene (Non-patent Documents 7, 10, 11, 12 and 13).

The WT1 gene product is present as a nuclear protein, and is processed by proteasomes in cytoplasm to be fragmented into peptides. The fragmented peptides are transported into endoplasmic reticulum lumen by TAP (transporter associated with antigen processing) molecules, form complexes with MHC class I molecules, and are presented on the surfaces of cells. WT1-specific CTLs are induced as a result of recognition of WT1 peptide-MHC class I molecule complexes by CTL precursor cells via TCR, thereby exerting a cytotoxic effect on tumor cells presenting a WT1 gene product through MHC class I molecules (Non-patent Documents 7, 8 and 9). Then, it is required at least that a WT1 peptide used in cancer immunotherapy targeting a WT1 gene product is in the form that binds to an MHC class I molecule in a living body. However, MHC class I molecules are diverse and amino acid sequences of the WT1 peptides binding to respective MHC class I molecules are different from each other. Therefore, it is required to provide a peptide matching each subtype of MHC class I. However, only HLA-A*2402 molecule-, HLA-A*0201 molecule-, HLA-A*2601 molecule- and HLA-A*3303 molecule-restricted peptides are known as HLA molecule-restricted WT1 peptides to date (Patent Document 1, Non-patent Document 11, Patent Document 2 and Patent Document 3, respectively). Thus, there is a need to find an HLA-A*1101-restricted WT1 peptide.

Patent Document 1: WO 2003/106682
Patent Document 2: WO 2005/095598
Patent Document 3: Japanese Patent Application No. 2006-45287
Non-patent Document 1: Daniel A. Haber et al., Cell. 1990 Jun. 29; 61(7):1257-69.
Non-patent Document 2: Call K M et al., Cell. 1990 Feb. 9; 60(3):509-20.
Non-patent Document 3: Menke A L et al., Int Rev Cytol. 1998; 181:151-212. Review.
Non-patent Document 4: Yamagami T et al., Blood. 1996 Apr. 1; 87(7):2878-84.
Non-patent Document 5: Inoue K et al., Blood. 1998 Apr. 15; 91(8):2969-76.
Non-patent Document 6: Tsuboi A et al., Leuk Res. 1999 May; 23(5):499-505.
Non-patent Document 7: Oka Y et al., J Immunol. 2000 Feb. 15; 164(4):1873-80.
Non-patent Document 8: Melief C J et al., Immunol Rev. 1995 June; 145:167-77.
Non-patent Document 9: Ritz J, J Clin Oncol. 1994 February; 12(2):237-8.
Non-patent Document 10: Tsuboi A et al., J Clin Immunol. 2000 May; 20(3):195-202.
Non-patent Document 11: Oka Y et al., Immunogenetics. 2000 February; 51(2):99-107.
Non-patent Document 12: Ohminami H et al., Blood. 2000 Jan. 1; 95(1):286-93.
Non-patent Document 13: Gao L et al., Blood. 2000 Apr. 1; 95(7):2198-203.

DISCLOSURE OF INVENTION

Problems to be Solved by the Invention

The problems to be solved by the present invention are to provide a peptide that is an HLA-A*1101 molecule-restricted and comprises an amino acid sequence from a WT1 protein, and a polynucleotide encoding the same, as well as a pharmaceutical composition for the treatment and/or prevention of a cancer, comprising the same, and the like.

Means to Solve the Problems

As a result of intensive studies in view of the situation as described above, the present inventor has found that among peptides each comprising an amino acid sequence consisting of 9 contiguous amino acids from a WT1 protein, peptides each having an ability to bind to an HLA-A*1101 molecule can induce a WT1-specific CTL with a high rate. Thus, the present invention has been completed.

The present invention provides:

(1) a peptide comprising an amino acid sequence consisting of 9 contiguous amino acids from a WT1 protein, wherein the peptide has an ability to bind to an HLA-A*1101 molecule, and has an ability to induce a CTL;

(2) the peptide according to (1), wherein the amino acid at position 9 of the amino acid sequence is Lys or Arg;

(3) the peptide according to (1), wherein the amino acid sequence is selected from the group consisting of:

```
                                         (SEQ ID No: 2)
    Ala Ala Gly Ser Ser Ser Ser Val Lys, (SEQ ID No: 3)
    Pro Ile Leu Cys Gly Ala Gln Tyr Arg, (SEQ ID No: 4)
    Arg Ser Ala Ser Glu Thr Ser Glu Lys, (SEQ ID No: 5)
    Ser Ala Ser Glu Thr Ser Glu Lys Arg, (SEQ ID No: 6)
    Ser His Leu Gln Met His Ser Arg Lys, (SEQ ID No: 7)
    Thr Gly Val Lys Pro Phe Gln Cys Lys, (SEQ ID No: 8)
    Lys Thr Cys Gln Arg Lys Phe Ser Arg, (SEQ ID No: 9)
    Ser Cys Arg Trp Pro Ser Cys Gln Lys,
    and (SEQ ID No: 10)
    Asn Met His Gln Arg Asn Met Thr Lys;
```

(4) the peptide according to (3), wherein the amino acid sequence is Ala Ala Gly Ser Ser Ser Ser Val Lys (SEQ ID No: 2);

(5) a peptide dimer having an ability to bind to an HLA-A*1101 molecule and having an ability to induce a CTL, in which two peptide monomers each comprising an amino acid sequence consisting of 9 contiguous amino acids from a WT1 protein, and comprising at least one cysteine residue are bound to each other through a disulfide bond;

(6) the peptide dimer according to (5), wherein the amino acid sequence of the peptide monomer is selected from the group consisting of:

```
                                         (SEQ ID No: 3)
    Pro Ile Leu Cys Gly Ala Gln Tyr Arg, (SEQ ID No: 7)
    Thr Gly Val Lys Pro Phe Gln Cys Lys,
```

```
-continued
                                         (SEQ ID No: 8)
    Lys Thr Cys Gln Arg Lys Phe Ser Arg,
    and (SEQ ID No: 9)
    Ser Cys Arg Trp Pro Ser Cys Gln Lys;
```

(7) a pharmaceutical composition for the treatment or prevention of a cancer, comprising the peptide according to (1) and/or the peptide dimer according to (5);

(8) a method for the treatment or prevention of a cancer, comprising administering an effective amount of the peptide according to (1) and/or the peptide dimer according to (5) to an HLA-A*1101-positive subject;

(9) a polynucleotide encoding the peptide according to (1);

(10) an expression vector comprising the polynucleotide according to (9);

(11) a pharmaceutical composition for the treatment or prevention of a cancer, comprising the polynucleotide according to (9) or the vector according to (10);

(12) a method for the treatment or prevention of a cancer, comprising administering an effective amount of the polynucleotide according to (9) or the vector according to (10) to an HLA-A*1101-positive subject;

(13) a WT1-specific CTL, which is induced by the peptide according to (1) and/or the peptide dimer according to (5);

(14) a method for the induction of a WT1-specific CTL, comprising culturing a peripheral blood mononuclear cell in the presence of the peptide according to (1) and/or the peptide dimer according to (5) to induce the WT1-specific CTL from the peripheral blood mononuclear cell;

(15) a kit for the induction of a WT1-specific CTL, comprising the peptide according to (1) and/or the peptide dimer according to (5) as an essential component;

(16) an antigen-presenting cell presenting a WT1 peptide, which is induced by the peptide according to (1) and/or the peptide dimer according to (5);

(17) a method for the induction of an antigen-presenting cell presenting a WT1 peptide, comprising culturing an immature antigen-presenting cell in the presence of the peptide according to (1) and/or the peptide dimer according to (5) to induce the antigen-presenting cell presenting a WT1 peptide from the immature antigen-presenting cell;

(18) a kit for the induction of an antigen-presenting cell presenting a WT1 peptide, comprising the peptide according to (1) and/or the peptide dimer according to (5) as an essential component; and

(19) a method for the diagnosis of a cancer, comprising using the CTL according to (13) or the antigen-presenting cell according to (16).

Effects of the Invention

The present invention provides a peptide that is HLA-A*1101-restricted and comprises an amino acid sequence consisting of 9 contiguous amino acids from a WT1 protein, and a polynucleotide encoding the same, as well as a pharmaceutical composition for the treatment and/or prevention of a cancer, comprising the same, and the like. Therefore, it is possible to induce in vivo and in vitro WT1-specific CTLs in subjects having HLA-A*1101. Because the rate of HLA-A*1101-positive in Japanese people is high (about 17.9%), WT1-specific CTLs can be induced in a wide range of subjects.

BRIEF DESCRIPTION OF DRAWINGS

FIG. 11 represents the cytotoxic activity of the CTL induced with WT1$_{378}$ peptide dimer (a and b represent the cytotoxic activities observed using PBMCs from HLA-A*1101-positive healthy donors 1 and 2, respectively).

BEST MODE FOR CARRYING OUT THE INVENTION

Figure 1:
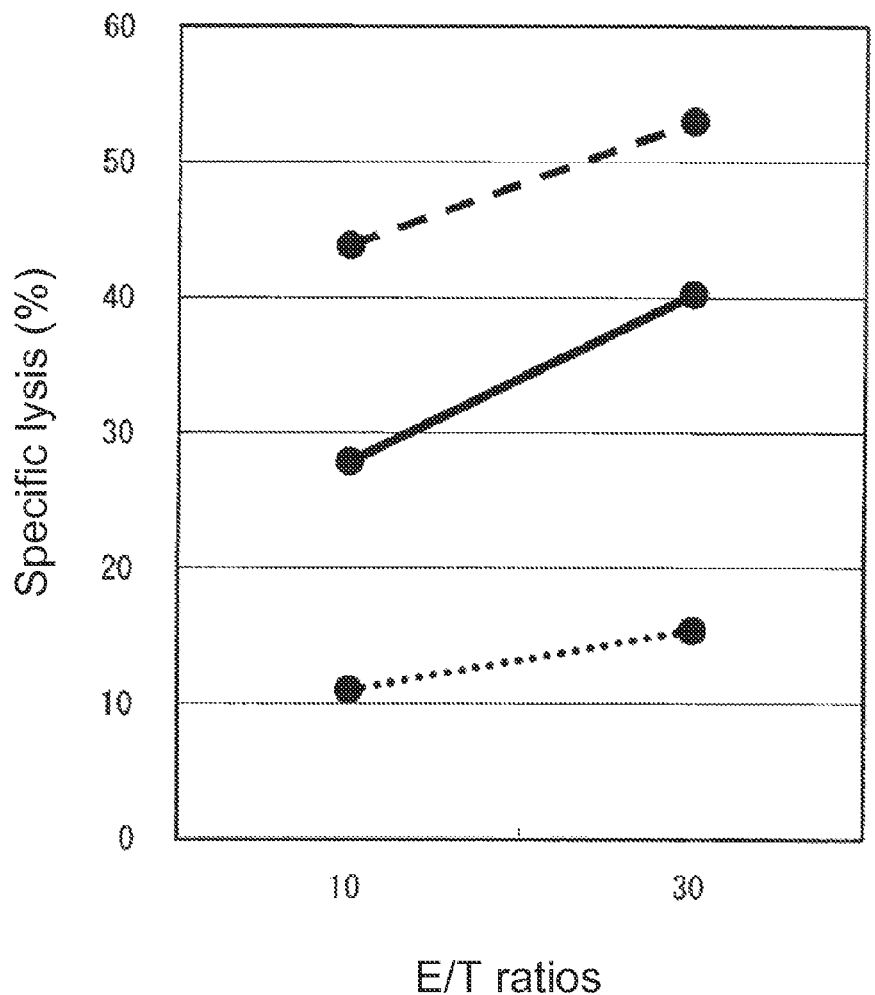
FIG. 1 represents the cytotoxic activity of the CTL induced with $WT1_{251}$.

In one aspect, the present invention relates to a peptide comprising an amino acid sequence consisting of 9 contiguous amino acids from a WT1 protein, wherein the peptide has an ability to bind to an HLA-A*1101 molecule, and has an ability to induce a CTL (herein also referred to as a "WT1 peptide"). The amino acid sequence of the human WT1 protein is shown in SEQ ID No: 1. The peptide of the present invention comprises an amino acid sequence consisting of 9 contiguous amino acids in the amino acid sequence shown in SEQ ID No: 1. When the peptide of the present invention comprises an amino acid sequence comprising cystein(s) such as the amino acid sequence of SEQ ID No: 3, 7, 8 or 9 as described below, the stability may be increased by substituting the cystein(s) in the amino acid sequence with another substance such as another amino acid (for example, serine, alanine and α-aminobutyric acid) or by modifying the SH group of the cystein(s) with a protecting group known in the art (for example, carboxymethyl group or pyridylethyl group). The peptide of the present invention is a cancer antigen peptide that can induce a CTL as a result of presentation, by an antigen-presenting cell, of a peptide generated by processing the peptide of the present invention in a cell.

As described above, it is an object of the present invention to obtain an HLA-A*1101-restricted peptide. Thus, the peptide of the present invention has an ability to bind to an HLA-A*1101 molecule. The ability to bind can be determined by a method known in the art. Examples of such methods include a computer-based method such as Rankpep, BIMAS or SYFPEITHI, and a competitive binding test with a known peptide having an ability to bind to an HLA-A*1101 molecule. For example, the determined ability to bind can be compared with that of a known HLA-A*1101-restricted peptide to judge whether or not the peptide of the present invention has an ability to bind. Examples of peptides having an ability to bind according to the present invention include a peptide of which the affinity score to an HLA-A*1101 molecule as determined by the method described in example 1 is 4 or more, preferably 5 or more, more preferably 6 or more.

The peptide of the present invention further has an ability to induce a CTL. The WT1 gene is expressed in its native form at high levels, for example, in hematopoietic tumors such as leukemia, myelodysplastic syndrome, multiple myeloma or malignant lymphoma and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer. Therefore, the peptide of the present invention can induce a CTL with a high rate in a subject suffering from such a disease. The ability to induce a CTL refers to an ability to induce a CTL in vivo or in vitro. Such an ability can be determined using a general method such as a method in which a cytotoxic activity of a CTL is determined using a Cr-release assay.

The peptide of the present invention may have Lys or Arg at position 9 of the amino acid sequence. It is considered that by having such an amino acid, the ability of the peptide to bind to an HLA-A*1101 molecule becomes higher.

The amino acid sequence consisting of 9 amino acids comprised in the peptide of the present invention is preferably, Ala Ala Gly Ser Ser Ser Ser Val Lys (SEQ ID No: 2), Pro Ile Leu Cys Gly Ala Gln Tyr Arg (SEQ ID No: 3), Arg Ser Ala Ser Glu Thr Ser Glu Lys (SEQ ID No: 4), Ser Ala Ser Glu Thr Ser Glu Lys Arg (SEQ ID No: 5), Ser His Leu Gln Met His Ser Arg Lys (SEQ ID No: 6), Thr Gly Val Lys Pro Phe Gln Cys Lys (SEQ ID No: 7), Lys Thr Cys Gln Arg Lys Phe Ser Arg (SEQ ID No: 8), Ser Cys Arg Trp Pro Ser Cys Gln Lys (SEQ ID No: 9) or Asn Met His Gln Arg Asn Met Thr Lys (SEQ ID No: 10). Most preferably, it is Thr Gly Val Lys Pro Phe Gln Cys Lys (SEQ ID No: 7). Furthermore, it may have a substitution of one to several, preferably one to five amino acids with other amino acids in the nine amino acids of any of SEQ ID Nos: 2-10. Any one of the 9 amino acids or other substituted amino acids may be appropriately modified. In any cases, the peptide of the present invention retains an ability to bind to an HLA-A*1101 molecule.

As described above, the peptide of the present invention may be any one as long as it comprises an amino acid sequence that is derived from a WT1 protein and consists of 9 contiguous amino acids. Thus, the peptide of the present invention may be, for example, a peptide consisting of only the amino acid sequence shown in any of SEQ ID Nos: 2-10, or a WT1 protein or a part thereof comprising the amino acid sequence shown in any of SEQ ID Nos: 2-10. The number of amino acids comprised in the peptide of the present invention is not specifically limited, and the number is, for example, 9-500, 9-300, 9-200, 9-100, 9-50, 9-30 and 9-12 amino acids. Various substances may be attached at the N-terminus and/or the C-terminus of the amino acid sequence consisting of 9 contiguous amino acids in the peptide of the present invention. For example, an amino acid, a peptide or an analog thereof may be attached. If such a substance is attached to the peptide of the present invention, the substance can be processed, for example, by an enzyme in a living body or through a process such as intracellular processing, and finally the amino acid sequence consisting of 9 contiguous amino acids can be produced and presented as a complex with an HLA-A*1101 molecule on the surface of a cell, thereby resulting in the effect of inducing a CTL. The substance may be a substance that modulates the solubility of the peptide of the present invention, or increases its stability (resistance to protease, etc.). Alternatively, it may be a substance that delivers the peptide of the present invention specifically, for example, to a given tissue or organ, or it may have an action to increase the efficiency of uptake by an antigen-presenting cell or the like. The substance may be a substance that increases an ability to induce a CTL, such as a helper peptide or the like.

The peptide of the present invention can be synthesized by methods generally used in the art or modifications thereof. Such methods are described, for example, in Peptide Synthesis, Interscience, New York, 1966; The Proteins, Vol 2, Academic Press Inc., New York, 1976; Peptide-Gosei, Maruzen Co., Ltd., 1975; Peptide-Gosei No Kiso To Jikken, Maruzen Co., Ltd., 1985; and Iyakuhin No Kaihatsu (Zoku), Vol. 14, Peptide-Gosei, Hirokawa—Book store, 1991.

The peptide of the present invention can also be prepared using genetic engineering techniques based on the information about the nucleotide sequence that encodes the peptide of the present invention. Such genetic engineering techniques are well known to a skilled person in the art.

In a further aspect, the present invention relates to a peptide dimer having an ability to bind to an HLA-A*1101 molecule and having an ability to induce a CTL, in which two peptide monomers each comprising an amino acid sequence consisting of 9 contiguous amino acids from a WT1 protein and comprising at least one cystein residue are bound to each other though a disulfide bond (hereinafter also referred to as a "WT1 peptide dimer"). The stability of the peptide dimer of the present invention is increased as compared with that of the peptide monomer by forming a dimer. The peptide dimer of the present invention is a tumor antigen peptide dimer that can induce a CTL as a result of presentation, by an antigen-presenting cell, of a peptide generated by processing the peptide of the present invention in a cell.

The peptide dimer of the present invention is formed by binding two peptide monomers through a disulfide bond between cystein residues present in the monomers. Thus, each of the peptide monomers comprised in the WT1 peptide dimer of the present invention is the WT1 peptide as described above and comprises at least one cystein residue. The WT1 peptide dimer of the present invention may be a homodimer or a heterodimer.

In the WT1 peptide dimer of the present invention, the amino acid sequence comprised by the peptide monomer comprises is preferably, Pro Ile Leu Cys Gly Ala Gln Tyr Arg (SEQ ID No: 3), Thr Gly Val Lys Pro Phe Gln Cys Lys (SEQ ID No: 7), Lys Thr Cys Gln Arg Lys Phe Ser Arg (SEQ ID No: 8) or Ser Cys Arg Trp Pro Ser Cys Gln Lys (SEQ ID No: 9). Most preferably, it is Thr Gly Val Lys Pro Phe Gln Cys Lys (SEQ ID No: 7).

The WT1 peptide dimer of the preset invention can be prepared using a method known in the art. For example, if the peptide monomers comprise one pair of cystein residues, the WT1 peptide dimer of the present invention can be prepared, for example, by removing all the protecting groups including the ones on the cystein side chains, and then subjecting the resulting monomer solution to air-oxidation under alkaline conditions, or adding an oxidant under alkaline or acidic conditions to form a disulfide bond. Examples of the oxidants include iodine, dimethylsulfoxide (DMSO) and potassium ferricyanide.

When each of the peptide monomers comprises two or more cystein residues, the WT1 peptide dimer of the present invention can also be prepared by the method as described above. In this case, isomers are obtained due to different types of disulfide bonds. Alternatively, the WT1 peptide dimer of the present invention can be prepared by selecting a combination of protecting groups for cystein side chains. Examples of the combinations of the protecting groups include combinations of MeBzl (methylbenzyl) group and Acm (acetamidemethyl) group, Trt (trityl) group and Acm group, Npys (3-nitro-2-pyridylthio) group and Acm group, and S-Bu-t (S-tert-butyl) group and Acm group. For example, in the case of the combination of MeBzl group and Acm group, the WT1 peptide dimer can be prepared by removing protecting groups other than the MeBzl group and the protecting group on the cystein side chain, subjecting the resulting monomer solution to air-oxidation to form a disulfide bond between the protected cystein residues, and then deprotecting and oxdizing using iodine to form a disulfide bond between the cystein residues previously protected by Acm.

In another aspect, the present invention relates to a pharmaceutical composition for the treatment or prevention of a cancer comprising the HLA-A*1101-restricted WT1 peptide and/or the WT1 peptide dimer. The WT1 gene is expressed at high levels in various cancers and tumors including hematopoietic tumors such as leukemia, myelodysplastic syndrome, multiple myeloma or malignant lymphoma and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer. Therefore, the pharmaceutical composition of the present invention can be used for the treatment or prevention of a cancer. When the pharmaceutical composition of the present invention is administered to an HLA-A*1101-positive subject, WT1-specific CTLs are induced by the HLA-A*1101-restricted WT1 peptide or the WT1 peptide dimer comprised in the pharmaceutical composition, and cancer cells in the subject are damaged by such CTLs.

The pharmaceutical composition of the present invention may comprise in addition to the HLA-A*1101-restricted WT1 peptide and/or the WT1 peptide dimer as an active ingredient, for example, a carrier, an excipient or the like. The HLA-A*1101-restricted WT1 peptide or the WT1 peptide dimer comprised in the pharmaceutical composition of the present invention induces a WT1-specific CTL. Thus, the pharmaceutical composition of the present invention may comprise an appropriate adjuvant, or may be administered together with an appropriate adjuvant in order to enhance the induction efficiency. Examples of preferable adjuvants include, but are not limited to, complete or incomplete Freund's adjuvant and aluminum hydroxide.

The method of the administration of the pharmaceutical composition of the present invention can be appropriately selected depending on conditions such as the type of disease, the condition of the subject or the target site. Examples of such methods include, but are not limited to, intradermal administration, subcutaneous administration, intramuscular administration, intravenous administration, nasal administration and oral administration. The amount of the peptide or the peptide dimer comprised in the pharmaceutical composition of the present invention, as well as the dosage form, the number of times of the administration and the like of the pharmaceutical composition of the present invention can be appropriately selected depending on conditions such as the type of disease, the condition of the subject or the target site. The single dose of the peptide is usually, 0.0001 mg-1000 mg, preferably, 0.001 mg-1000 mg.

In another aspect, the present invention relates to a method for the treatment or prevention of a cancer, comprising administering an effective amount of the WT1 peptide and/or the WT1 peptide dimer to an HLA-A*1101-positive subject. The cancer to be treated or prevented may be any one, and examples thereof include hematopoietic tumors such as leukemia, myelodysplastic syndrome, multiple myeloma or malignant lymphoma and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer.

In a further aspect, the present invention relates to a method for the determination of the presence or amount of a WT1-specific CTL in an HLA-A*1101-positive subject, comprising:

(a) reacting a complex of a WT1 peptide and an HLA-A*1101 molecule with a sample from the subject; and
(b) determining the presence or amount of a CTL recognizing the complex contained in the sample. The sample from a subject may be any one as long as there is a possibility that it contains a lymphocyte. Examples of the samples include body fluid such as blood or lymph and a tissue. The complex of a WT1 peptide and an HLA-A*1101 molecule may be prepared, for example, as a tetramer or pentamer using a method known to a skilled person in the art such as biotin-streptavidin method. The presence or amount of the CTL recognizing such a complex can be measured by a method known to a skilled person in the art. In this aspect of the present invention, the complex may be labeled. A known label such as a fluorescent label or a radioactive label can be used as a label. Labeling makes the determination of the presence or amount of a CTL easy and rapid.

Thus, the present invention also provides a composition for the determination of the presence or amount of a WT1-specific CTL in an HLA-A*1101-positive subject comprising an HLA-A*1101-restricted WT1 peptide.

Furthermore, the present invention provides a kit for the determination of the presence or amount of a WT1-specific CTL in an HLA-A*1101-positive subject, comprising an HLA-A*1101-restricted WT1 peptide.

In a further aspect, the present invention relates to a method for the production of a WT1-specific CTL using a complex of a WT1 peptide and an HLA-A*1101 molecule, comprising:

(a) reacting the complex with a sample; and
(b) obtaining a CTL recognizing the complex contained in the sample. The complex of a WT1 peptide and an HLA-A*1101 molecule is described above. The sample may be any one as long as there is a possibility that it contains a lymphocyte. Examples of the samples include a sample from a subject such as blood, and a cell culture. The CTL recognizing the complex can be obtained using a method known to a skilled person in the art such as FACS or MACS. The present invention allows to culture the obtained WT1-specific CTL and use it for the treatment or prevention of various cancers.

Thus, the present invention also relates to a WT1-specific CTL obtainable by a method for the production of a WT1-specific CTL using a complex of a WT1 peptide and an HLA-A*1101 molecule.

In another aspect, the present invention relates to a polynucleotide encoding the HLA-A*1101-restricted WT1 peptide. The polynucleotide of the present invention may be DNA or RNA. The base sequence of the polynucleotide of the present invention can be determined based on the amino acid sequence of the HLA-A*1101-restricted WT1 peptide. The polynucleotide can be prepared by a known method for the synthesis of DNA or RNA (for example, chemical synthetic method), PCR method or the like.

In another aspect, the present invention relates to an expression vector comprising the polynucleotide. The type of the expression vector, the comprised sequence other than the sequence of the polynucleotide and the like can be appropriately selected depending on the type of a host into which the expression vector of the present invention is introduced, the purpose of use, or the like. It is possible to treat or prevent hematopoietic tumors or solid cancers by administering the expression vector of the present invention to an HLA-A*1101-positive subject to produce an HLA-A*1101-restricted WT1 peptide in a living body and induce a WT1-specific CTL, and damaging hematopoietic tumor cells or solid cancer cells in the subject.

In a further aspect, the present invention relates to a pharmaceutical composition for the treatment or prevention of a cancer, comprising the polynucleotide or the expression vector. The composition, method of the administration and the like of the pharmaceutical composition of the present invention in this aspect are described above.

In another aspect, the present invention relates to a method for the treatment or prevention of a cancer, comprising administering an effective amount of the polynucleotide or the expression vector to an HLA-A*1101-positive subject. Examples of cancers to be treated or prevented include hematopoietic tumors such as leukemia, myelodysplastic syndrome, multiple myeloma or malignant lymphoma and solid cancers such as gastric cancer, colon cancer, lung cancer, breast cancer, germ cell cancer, hepatic cancer, skin cancer, bladder cancer, prostate cancer, uterine cancer, cervical cancer or ovarian cancer.

In another aspect, the present invention relates to a cell comprising the expression vector. The cell of the present invention can be prepared, for example, by transforming a host cell such as *E. coli*, yeast, insect cell or animal cell with the expression vector. The method for the introduction of the expression vector into a host cell can be appropriately selected from various methods. By culturing the transformed cell, and recovering and purifying the produced WT1 peptide, the peptide of the present invention can be prepared.

In a further aspect, the present invention relates to a WT1-specific CTL, which is induced by the HLA-A*1101-restriceted WT1 peptide and/or the WT1 peptide dimer. The CTL of the present invention recognizes a complex of a WT1 peptide and an HLA-A*1101 molecule. Thus, the CTL of the present invention can be used to damage specifically a tumor cell positive for HLA-A*1101 and expressing WT1 at a high level.

In another aspect, the present invention relates to a method for the treatment or prevention of a cancer, comprising administering a WT1-specific CTL to an HLA-A*1101-positive subject. The method of the administration of the WT1-specific CTL can be appropriately selected depending on conditions such as the type of the disease, the condition of the subject or the target site. Examples of such methods include, but are not limited to, intravenous administration, intradermal administration, subcutaneous administration, intramuscular administration, nasal administration and oral administration.

In another aspect, the present invention relates to a method for the induction of a WT1-specific CTL, comprising culturing a peripheral blood mononuclear cell in the presence of the HLA-A*1101-restricted WT1 peptide and/or the WT1 peptide dimer to induce the WT1-specific CTL form the peripheral blood mononuclear cell. The subject from which the peripheral blood mononuclear cell is derived may be any one as long as it is positive for HLA-A*1101. By culturing the peripheral blood mononuclear cells in the presence of the HLA-A*1101-restricted WT1 peptide and/or the WT1 peptide dimer, WT1-specific CTLs are induced from CTL precursor cells contained in the peripheral blood mononuclear cells. It is possible to treat or prevent hematopoietic tumors or solid cancers in an HLA-A*1101-positive subject by administering the WT1-specific CTL obtained according to the present invention to the subject.

In another aspect, the present invention relates to a kit for the induction of a WT1-specific CTL, comprising an HLA-A*1101-restricted WT1 peptide and/or the WT1 peptide dimer as an essential component. Preferably, the kit is used in the method for the induction of a WT1-specific CTL. The kit of the present invention may comprise in addition to the HLA-A*1101-restricted WT1 peptide and/or the WT1 peptide dimer, for example, a means of obtaining a peripheral blood mononuclear cell, an adjuvant, a reaction vessel or the like. In general, an instruction manual is attached to the kit. By using the kit of the present invention, WT1-specific CTLs can be induced efficiently.

In a further aspect, the present invention relates to an antigen-presenting cell (such as a dendritic cell) presenting a WT1 peptide through an HLA-A*1101 molecule, which is induced by the HLA-A*1101-restricted WT1 peptide and/or the WT1 peptide dimer. By using the antigen-presenting cell of the present invention, WT1-specific CTLs are induced efficiently.

In another aspect, the present invention relates to a method for the treatment or prevention of a cancer, comprising administering the antigen-presenting cell presenting a WT1 peptide through an HLA-A*1101 molecule to an HLA-A*1101-positive subject. The method of the administration of the antigen-presenting cell can be appropriately selected depending on conditions such as the type of the disease, the condition of the subject or the target site. Examples of such methods include, but are not limited to, intravenous administration, intradermal administration, subcutaneous administration, intramuscular administration, nasal administration and oral administration.

In another aspect, the present invention relates to a method for the induction of an antigen-presenting cell presenting a WT1 peptide through an HLA-A*1101 molecule, comprising culturing an immature antigen-presenting cell in the presence of the HLA-A*1101-restricted WT1 peptide and/or the WT1 peptide dimer to induce the antigen-presenting cell presenting a WT1 peptide through an HLA-A*1101 molecule from the immature antigen-presenting cell. The immature antigen-presenting cell refers a cell such as an immature dendritic cell that can be matured into an antigen-presenting cell. A subject from which the immature antigen-presenting cell is derived may be any one as long as it is positive for HLA-A*1101. Because the immature antigen-presenting cells are contained, for example, in peripheral blood mononuclear cells, such cells may be cultured in the presence of the WT1 peptide and/or the WT1 peptide diemr.

In another aspect, the present invention relates to a kit for the induction of an antigen-presenting cell presenting a WT1 peptide through an HLA-A*1101 molecule, comprising the HLA-A*1101-restricted WT1 peptide and/or the WT1 peptide as an essential component. Preferably, the kit is used in the method for the induction of an antigen-presenting cell. Another component to be comprised in the kit of the present invention and the like are described above. The kit of the present invention can be used to induce efficiently an antigen-presenting cell presenting a WT1 peptide through an HLA-A*1101 molecule.

In another aspect, the present invention relates to an antibody against an HLA-A*1101-restricted WT1 peptide or a polynucleotide encoding the peptide. The antibody of the present invention may be a polyclonal antibody or monoclonal antibody.

In a further aspect, the present invention relates to a method for the diagnosis of a cancer, comprising using the WT1-specific CTL, the antigen-presenting cell presenting a WT1 peptide through an HLA-A*1101 molecule, or the antibody against an HLA-A-restricted WT1 peptide or a polynucleotide encoding the peptide. Preferably, the WT1-specific CTL is used in the method for the diagnosis of the present invention. For example, it is possible to diagnose a cancer by incubating the CTL, the antigen-presenting cell or the antibody with a sample from an HLA-A*1101-positive subject, or administering it to an HLA-A*1101-positive subject, and determining, for example, the position, site or amount thereof. The CTL, the antigen-presenting cell or the antibody may be labeled. By attaching a label, the method for the diagnosis of the present invention can be practiced efficiently.

EXAMPLES

The following examples illustrate the present invention in more detail, but are not to be construed to limit the scope thereof.

Example 1

Selection of WT1 Peptide

RANKPEP (bio.dfci.harvard.edu/Tools/rankpep.html) was used to select $WT1_{251}$, $WT1_{279}$, $WT1_{312}$, $WT1_{313}$, $WT1_{338}$, $WT1_{378}$, $WT1_{386}$, $WT1_{415}$ and $WT1_{436}$ having a high ability to bind to an HLA-A*1101 molecule derived from peptides from a WT1 protein (SEQ ID No: 1). Amino acid sequences, amino acid numbers in SEQ ID No: 1 and affinity scores to an HLA-A*1101 molecule of these peptides are shown in Table 1.

TABLE 1

| Peptide | Amino acid Number | Amino acid sequence | Affinity score |
|---|---|---|---|
| $WT1_{251}$ (SEQ ID No: 2) | 251-259 | AAGSSSSVK | 15.18 |
| $WT1_{279}$ (SEQ ID No: 3) | 279-287 | PILCGAQYR | 11.47 |
| $WT1_{312}$ (SEQ ID No: 4) | 312-320 | RSASETSEK | 14.96 |
| $WT1_{313}$ (SEQ ID No: 5) | 313-321 | SASETSEKR | 6.87 |
| $WT1_{338}$ (SEQ ID No: 6) | 338-346 | SHLQMHSRK | 13.72 |
| $WT1_{378}$ (SEQ ID No: 7) | 378-386 | TGVKPFQCK | 11.33 |
| $WT1_{386}$ (SEQ ID No: 8) | 386-394 | KTCQRKFSR | 13.82 |
| $WT1_{415}$ (SEQ ID No: 9) | 415-423 | SCRWPSCQK | 10.29 |
| $WT1_{436}$ (SEQ ID No: 10) | 436-444 | NMHQRNMTK | 14.19 |

Preparation of B-LCL Cell

Peripheral blood mononuclear cells (PBMCs) were separated by Ficoll-Hypaque gradient density centrifugation method from peripheral blood that had been collected from an HLA-A*1101-positive healthy donor. The PBMCs were then seeded to a 24-well cell culture plate at the density of about $1 \times 10^7$ in RPMI 1640 medium containing 10% FCS, and a culture supernatant of B95-8 cells (cells producing EB virus) were added. They were cultured at 37° C. with 5% $CO_2$ for about 1 month. B-LCL cells transformed with EB virus, which are B-cell tumor cells, were obtained. It was confirmed that the resulting B-LCL cells did not express WT1 gene. B-LCL cells were pulsed by incubating them with 20 μg/ml of $WT1_{251}$, $WT1_{279}$, $WT1_{312}$, $WT1_{313}$, $WT1_{338}$, $WT1_{378}$, $WT1_{386}$, $WT1_{415}$ or $WT1_{436}$ for 2 hours, and irradiated with 80 Gy of radiation. The resulting B-LCL cells (hereinafter referred to as B-LCL cells pulsed with a WT1 peptide) were used as antigen-presenting cells for the following experiments.

Induction of WT1-Specific CTL $3 \times 10^6$ of autologous PBMCs were cultured in a 24-well cell culture plate in complete medium (45% RPMI, 45% AMI-V medium and 10% human AB serum) containing 20 μg/ml of $WT1_{251}$, $WT1_{279}$, $WT1_{312}$, $WT1_{313}$, $WT1_{338}$, $WT1_{378}$, $WT1_{386}$, $WT1_{415}$ or $WT1_{436}$ at 37° C. with 5% $CO_2$ for 1 week to obtain responding cells. $2 \times 10^6$ of the resulting responding cells were cocultured with $1 \times 10^6$ of the B-LCL cells pulsed with the same WT1 peptide in complete medium for 1 week (first stimulation). The PBMCs were cocultured with the B-LCL cells pulsed with the WT1 peptide three more times (second to fourth stimulations) under the conditions under which 20 IU/ml (final concentration) of IL2 was added as follows: second stimulation: two times every other day from 3 days after the initiation of stimulation; third and fourth stimulations: three times at intervals of one day from the day after the initiation of stimulation. The resulting cells were concentrated using Negative Selection Columns Gravity Feed Kit (StemSp) so that the ratio of CD8-positive T cells became about 80%, and cocultured with the B-LCL cells pulsed with the WT1 peptide (fifth stimulation). CD8-positive T cells (CTLs) obtained 5 days after the final stimulation were used for measurement of the cytotoxic activity.

Cytotoxic Activity of CTL

Figure 2:
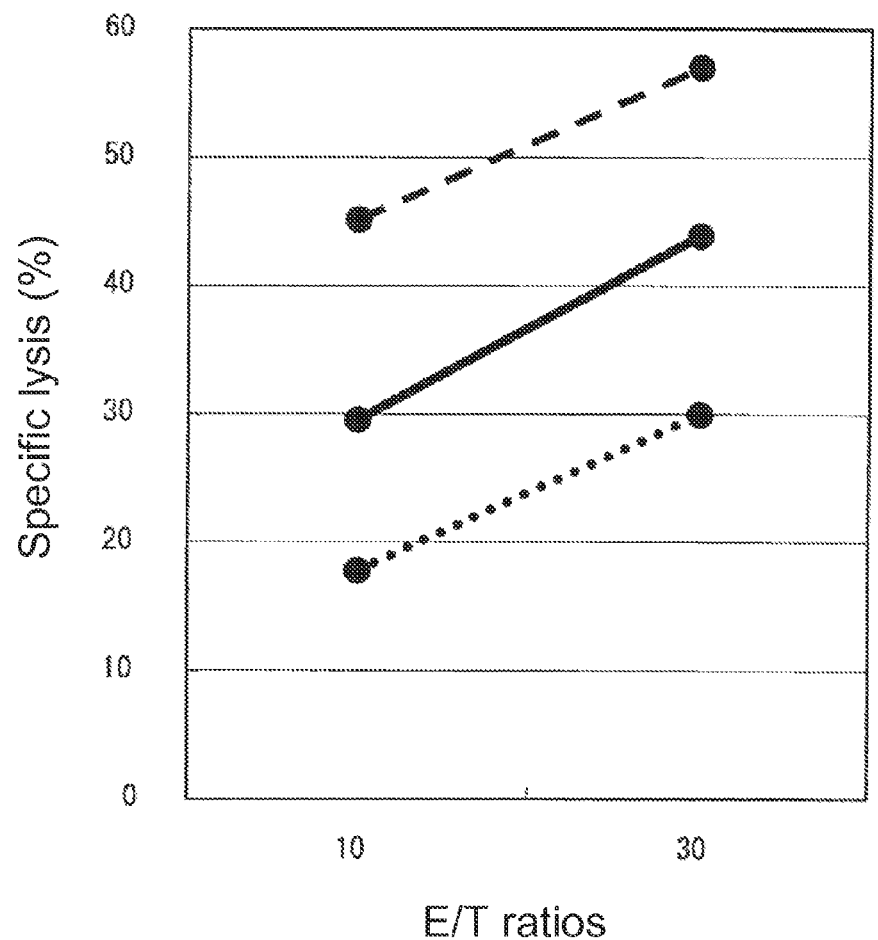
FIG. 2 represents the cytotoxic activity of the CTL induced with WT1$_{279}$.
Figure 3:
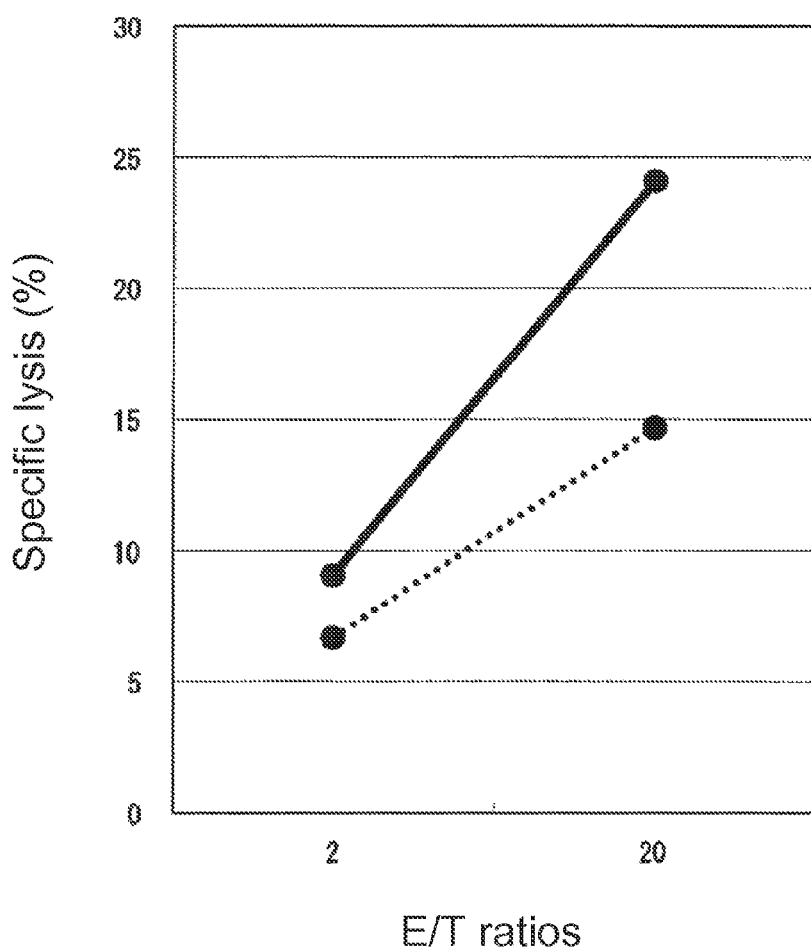
FIG. 3 represents the cytotoxic activity of the CTL induced with WT1$_{312}$.
Figure 4:
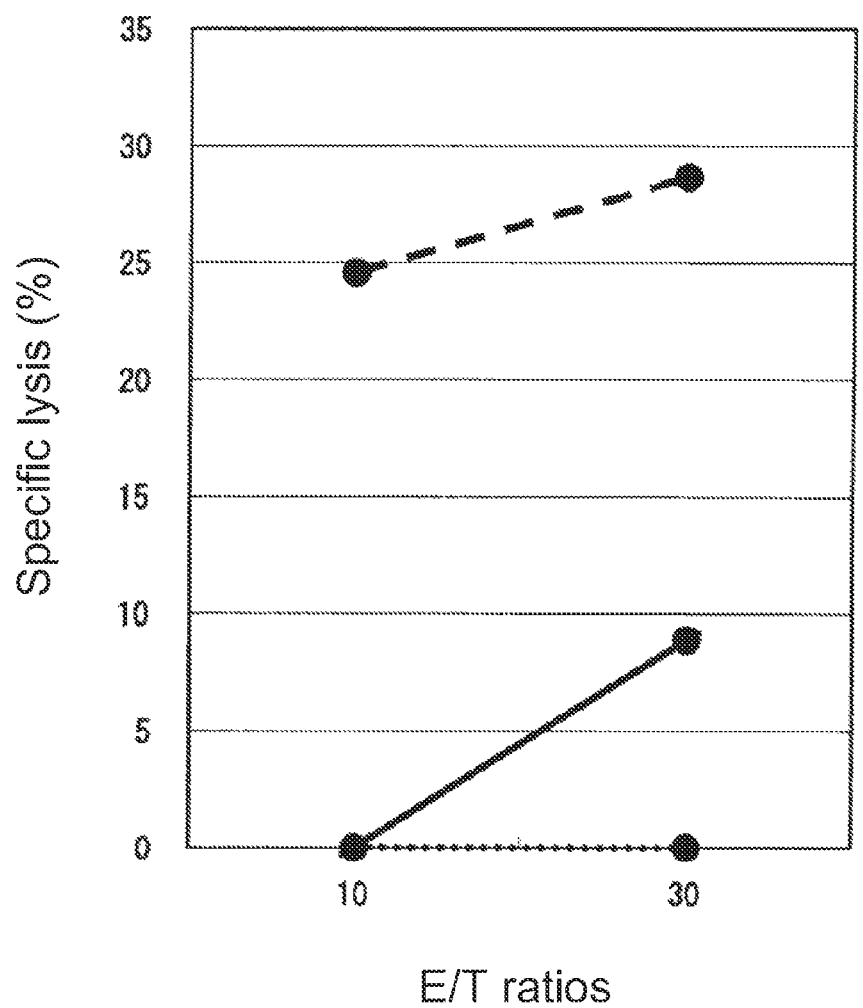
FIG. 4 represents the cytotoxic activity of the CTL induced with WT1$_{313}$.
Figure 5:
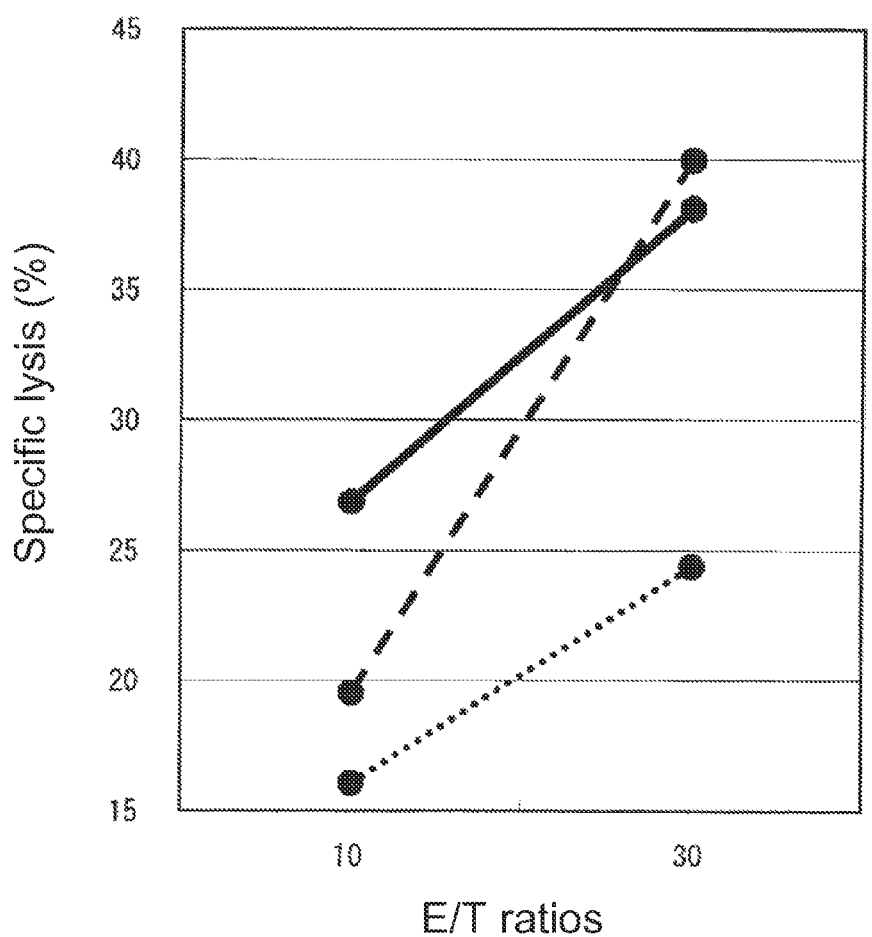
FIG. 5 represents the cytotoxic activity of the CTL induced with WT1$_{338}$.
Figure 6:
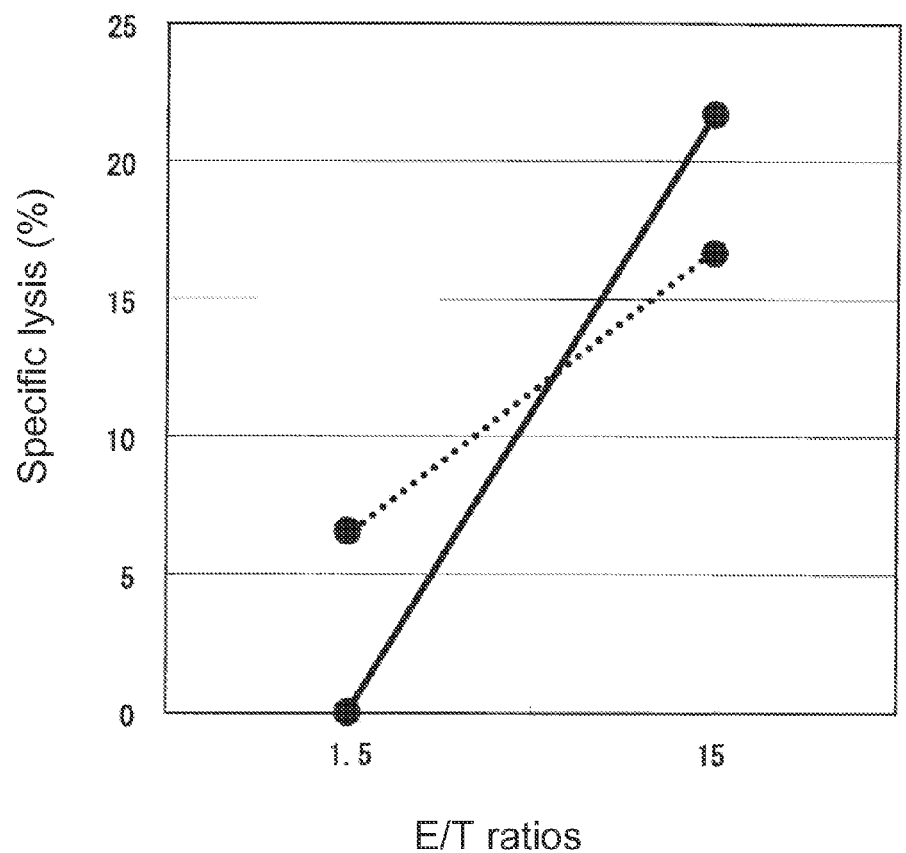
FIG. 6 represents the cytotoxic activity of the CTL induced with WT1$_{378}$.
Figure 7:
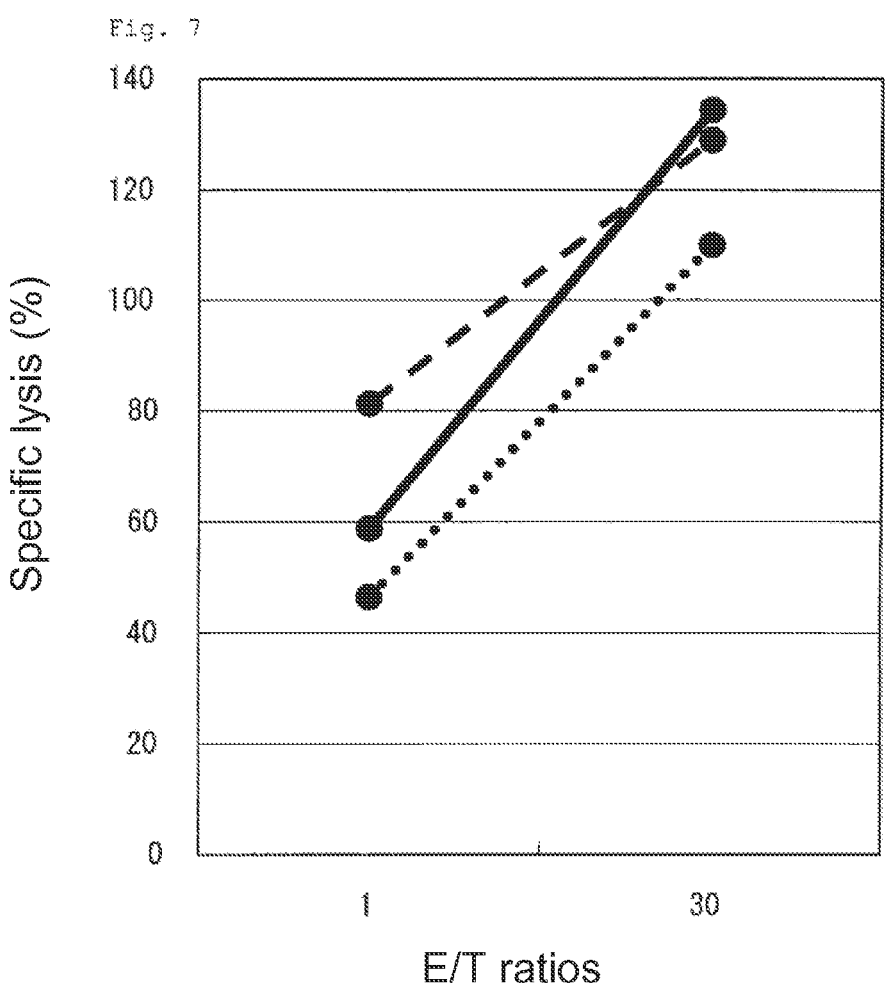
FIG. 7 represents the cytotoxic activity of the CTL induced with WT1$_{386}$.
Figure 8:
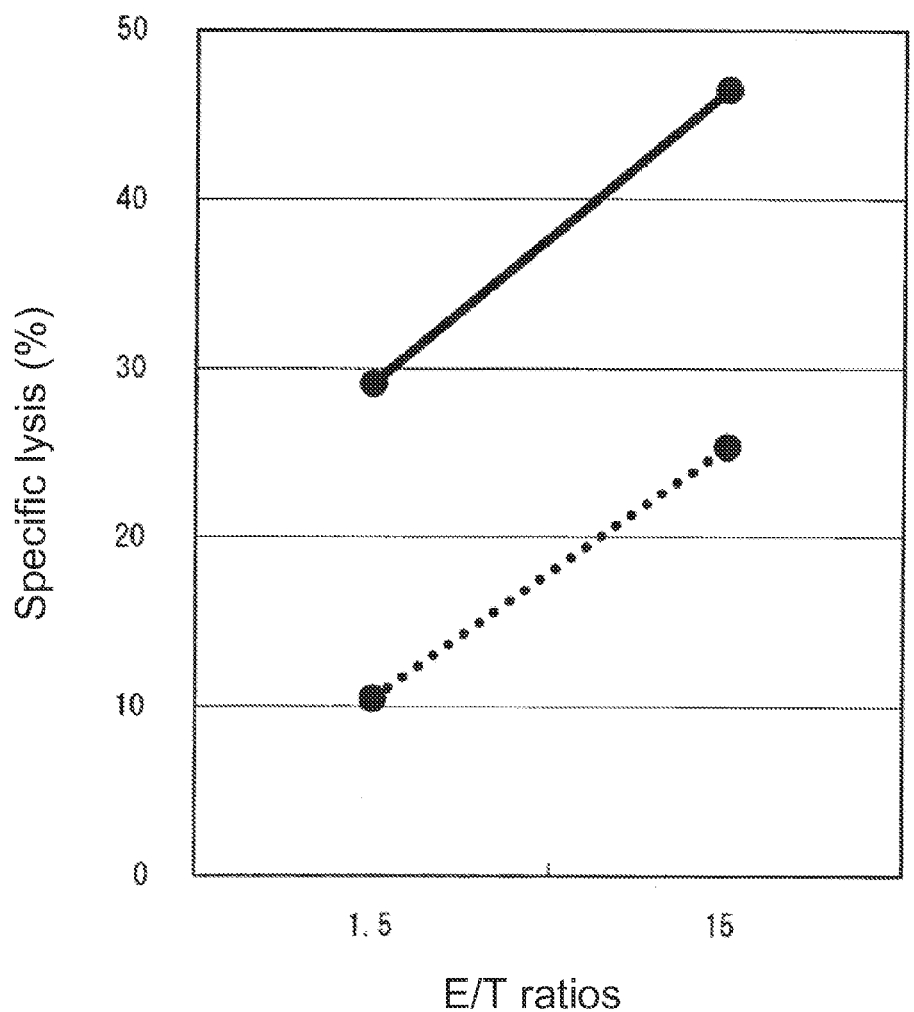
FIG. 8 represents the cytotoxic activity of the CTL induced with WT1$_{415}$.
Figure 9:
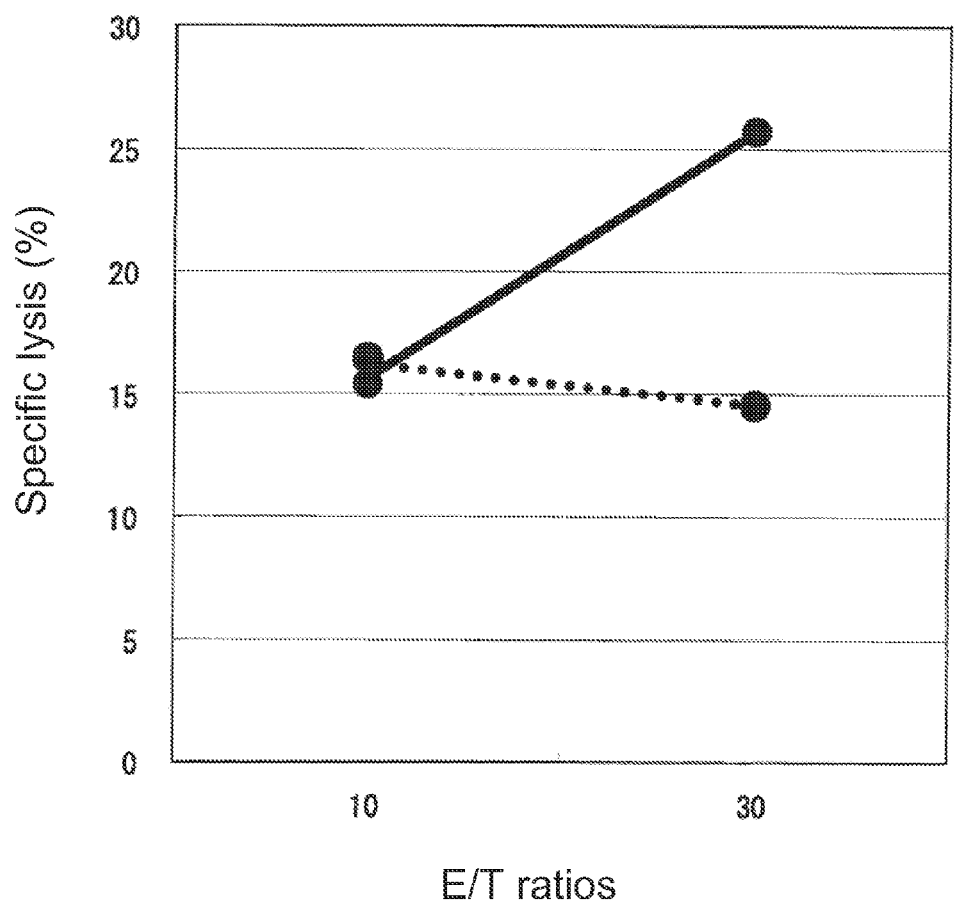
FIG. 9 represents the cytotoxic activity of the CTL induced with WT1$_{436}$.

The cytotoxic activity of CTLs was measured using $^{51}Cr$ release assay. CTL cells (hereinafter referred to as effector cells) were mixed at the ratio (E/T ration) of 1:1 to 30:1 in 200 μl of medium with target cells into which $^{51}Cr$ had been incorporated, and cultured in a 96-well cell culture plate at 37° C. with 5% $CO_2$ for 4 hours. B-LCL cells pulsed with the same WT1 peptide as that used for induction of CTLs (BLCL-Ps), and B-LCL cells without pulsing with a WT1 peptide (BLCL-NPs) were used as target cells. After the culture, the supernatants were collected by centrifugation. The amounts of $^{51}Cr$ released into the supernatants were measured using a liquid scintillation counter. The cytotoxic activity (%) was determined using the following formula:

($^{51}$Cr release in supernatant of sample–Spontaneous $^{51}$Cr release)/(Maximum $^{51}$Cr release–Spontaneous $^{51}$Cr release)×100 wherein Spontaneous $^{51}Cr$ release is $^{51}Cr$ release observed when the target cells into which $^{51}Cr$ had been incorporated were cultured alone under the same condition, and Maximum $^{51}Cr$ release is $^{51}Cr$ release observed when the target cells into which $^{51}Cr$ had been incorporated were completely lysed using 1% Triton X-100. Results are shown in FIGS. 1-9. In the figures, longitudinal axes represent specific lysis (%), and horizontal axes represent E/T ratios. BLCL-Ps are represented using full lines, and BLCL-NPs are represented using dotted lines. It was confirmed that CTLs induced with $WT1_{251}$, $WT1_{279}$, $WT1_{312}$, $WT1_{313}$, $WT1_{338}$, $WT1_{378}$, $WT1_{386}$, $WT1_{415}$ or $WT1_{436}$ damage specifically BLCL-Ps presenting the WT1 peptide as a complex with an HLA-A*1101 molecule as compared with BLCL-NPs. CTLs induced with $WT1_{251}$, $WT1_{279}$, $WT1_{313}$, $WT1_{338}$ or $WT1_{386}$ were used for additional experiments below.

Cytotoxic Activity of CTL Against Cell Expressing WT1 Endogenously

The cytotoxic activity of CTLs induced with $WT1_{251}$, $WT1_{279}$, $WT1_{313}$, $WT1_{338}$ or $WT1_{386}$ against B-LCLs expressing WT1 was determined using the method described above. A cell expressing WT1 refers to a B-LCL into which a human WT1 gene is introduced, and that expresses a WT1 protein in the cell, and presents a peptide consisting of about 9 amino acids resulting from processing on an HLA-A*1101 molecule. Results are shown in FIGS. 1, 2, 4, 5 and 7. In the figures, B-LCLs expressing WT1 are represented using dashed lines. It was confirmed that CTLs induced with $WT1_{251}$, $WT1_{279}$, $WT1_{313}$, $WT1_{338}$ or $WT1_{386}$ have a cytotoxic activity against cells expressing WT1 gene endogenously.

Preparation of WT1 Peptide Dimer

A mixture of 227.5 mg of $WT1_{378}$ peptide monomer, 227.5 mg of N-methylglucamine (NMG) and 23 ml of water was air-oxidized by stirring at room temperature for about 2 days. To the resulting mixture, an aqueous solution of 2 g of sodium acetate in 5 ml of water was added and the mixture was stirred at room temperature for about 20 minutes. To the resulting solution, 200 ml of water and about 200 ml of acetonitrile were added, and the mixture was filtered through Kiriyama funnel (filter paper No. 5C) and washed with water (about 50 ml×3). To the residue, about 200 ml of water was added and the residue was lyophilized to obtain 158 mg of crude $WT1_{378}$ peptide dimer.

Purification of Crude WT1 Peptide Dimer 158 mg of the crude $WT1_{378}$ peptide dimer was dissolved in 9 ml of DMSO and injected into ODS $C_{18}$ column (5 cm Φ×50 cm L, YMC Co., LTD.) attached to HPLC (Shimadzu, LC8AD type) and equilibrated with solution 1 ($H_2O$/ 1% AcOH) using a HPLC pump. The column was left for about 30 minutes, and eluted with concentration gradient of 0% to 40% of solution 2 ($CH_3CN$/1% AcOH) over 360 minutes. The fractions containing WT1 peptide dimer were collected using an automatic fraction collector while monitoring UV absorbance at 220 nm. The collected fractions were combined, injected into ODS $C_{18}$ column (4.6 mm Φ×25 cm L, YMC Co., LTD.) attached to HPLC (Hitachi, L-4000 type) and equilibrated with 17% of solution 2, and eluted with concentration gradient of 0% to 47% of solution 2 over 30 minutes to obtain 46.6 mg of the purified $WT1_{378}$ peptide dimer at retention time of 20.51 minutes. FAB.MS 2365.0 (theoretical value: 2342.70) Na+ F=0.25%

Induction of CTL by WT1 Peptide Dimer

Figure 10:
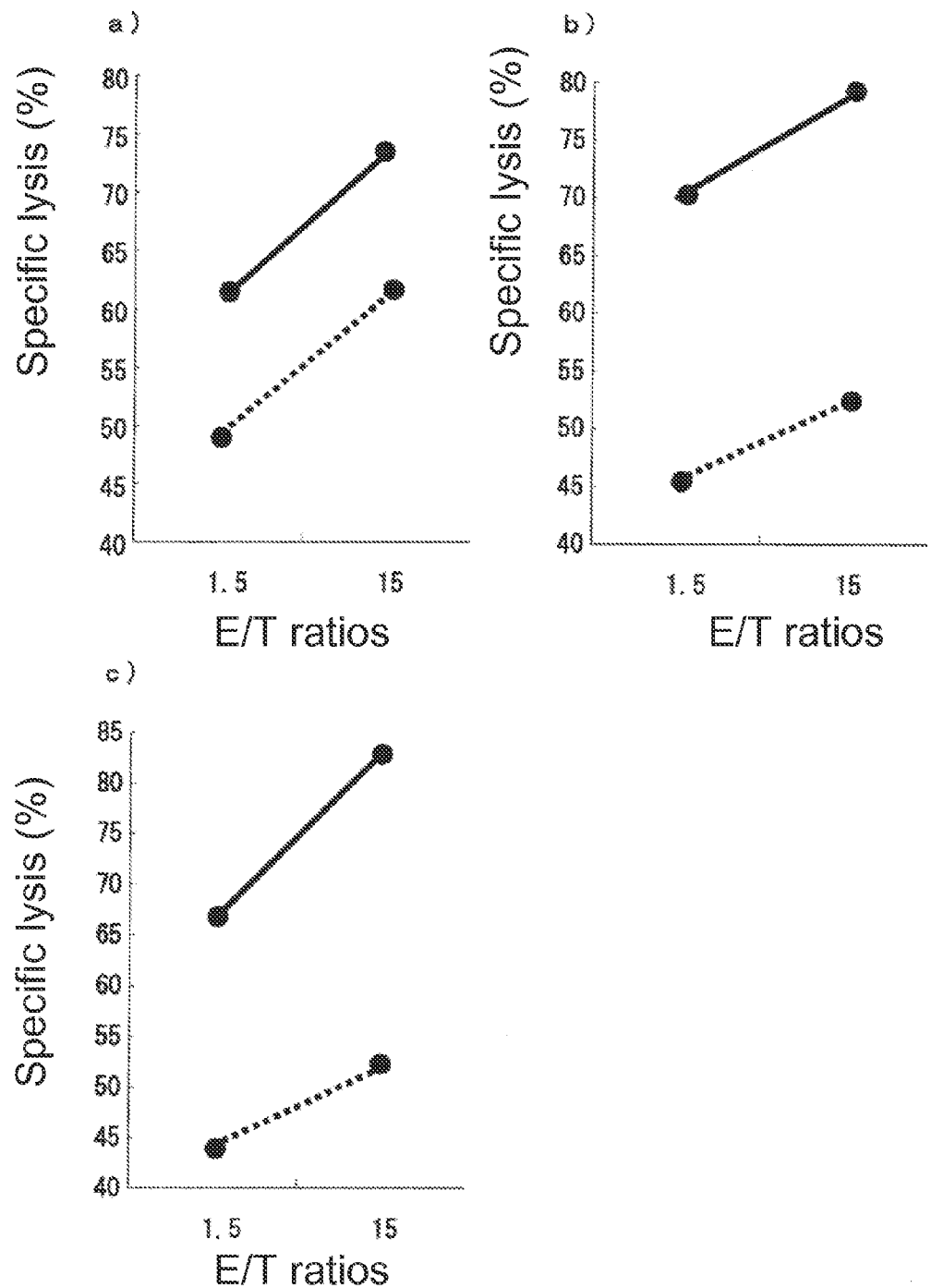
FIG. 10 represents the cytotoxic activity of the CTL induced with WT1$_{378}$ peptide (a, b and c represent the cytotoxic activities observed using PBMCs from HLA-A*1101-positive healthy donors 1, 2 and 3, respectively).
Figure 12:
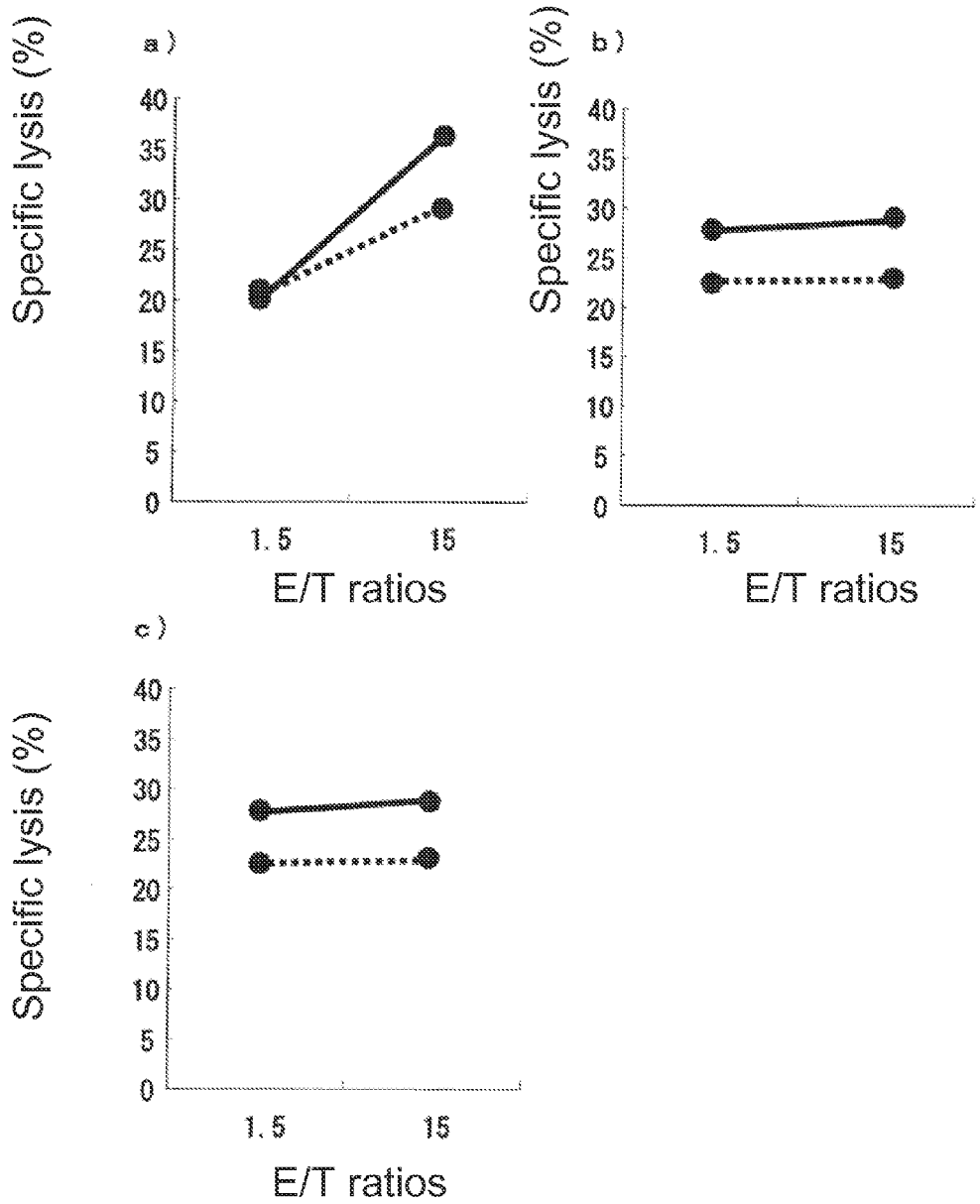
FIG. 12 represents the cytotoxic activity of the CTL induced with modified WT1$_{378}$ peptide (G→I) (a, b and c represent the cytotoxic activities observed using PBMCs from HLA-A*1101-positive healthy donors 1, 2 and 3, respectively).
Figure 13:
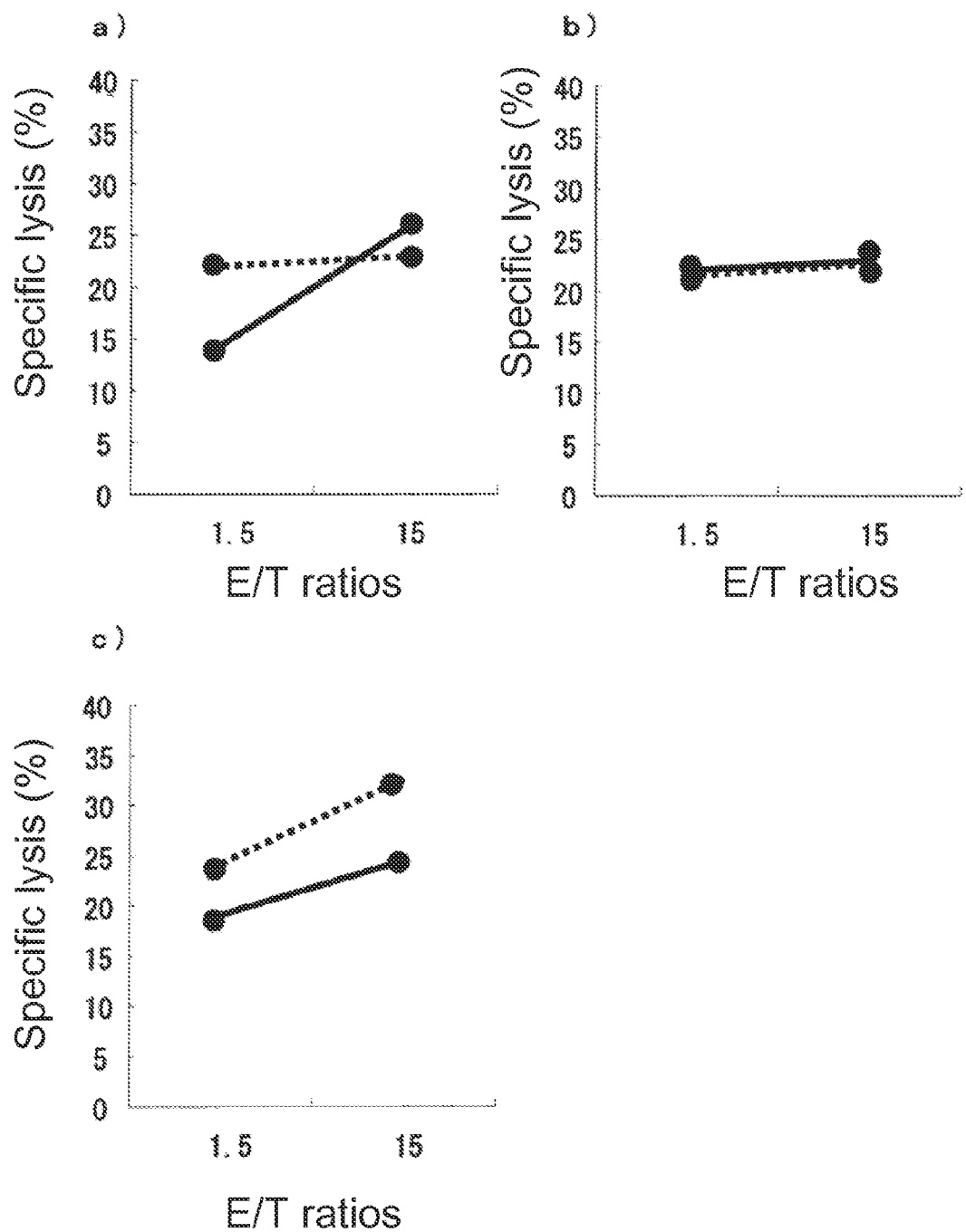
FIG. 13 represents the cytotoxic activity of the CTL induced with modified WT1$_{378}$ peptide (G→V) (a, b and c represent the cytotoxic activities observed using PBMCs from HLA-A*1101-positive healthy donors 1, 2 and 3, respectively).
Figure 14:
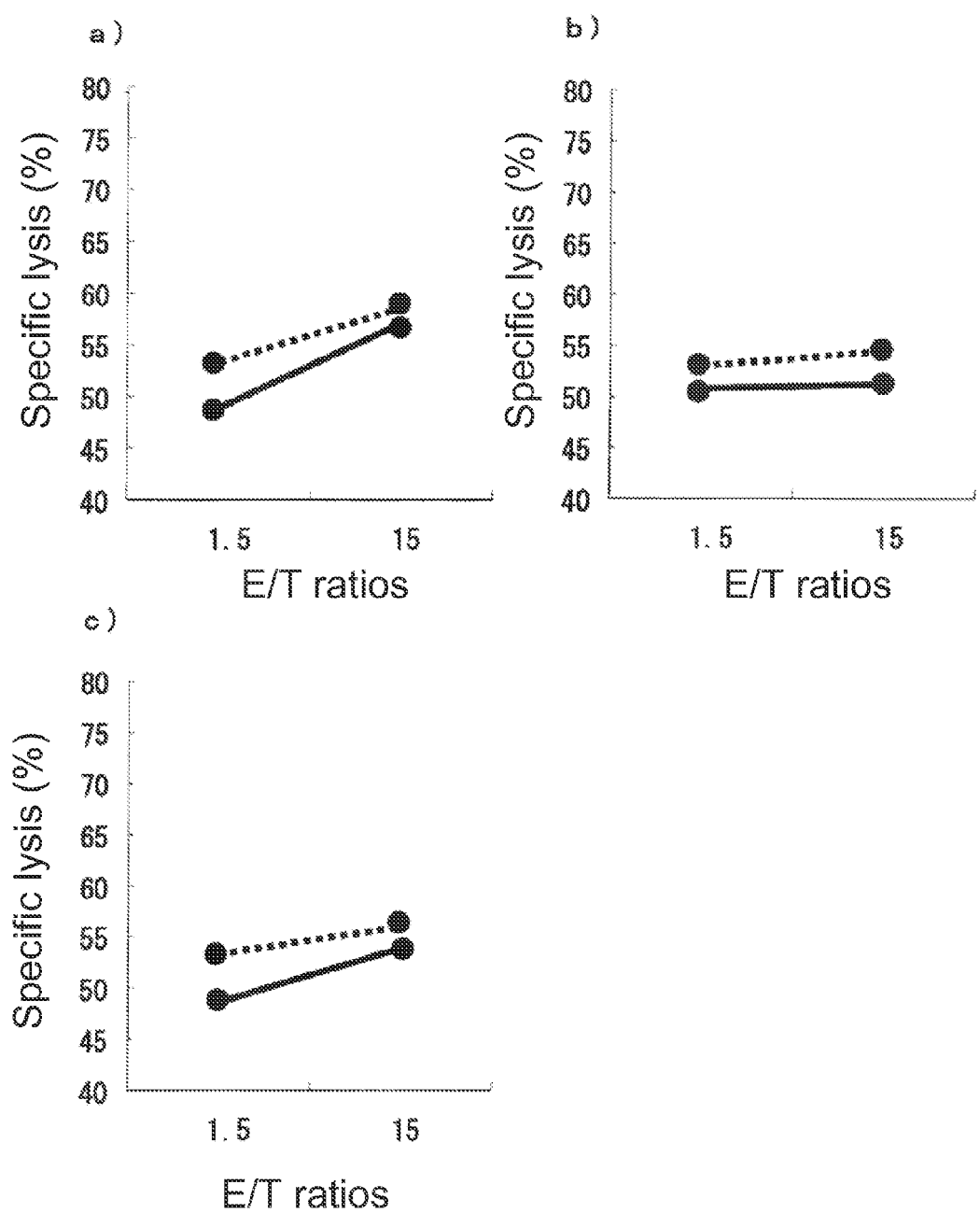
FIG. 14 represents the cytotoxic activity of the CTL induced with WT1$_{379}$ peptide (a, b and c represent the cytotoxic activities observed using PBMCs from HLA-A*1101-positive healthy donors 1, 2 and 3, respectively).

Abilities of the resulting $WT1_{378}$ peptide dimer, $WT1_{378}$ peptide, modified $WT1_{378}$ peptide (G I) (SEQ ID No: 11) and modified $WT1_{378}$ peptide (G→V) (SEQ ID No: 12) as well as $WT1_{379}$ peptide (SEQ ID No: 13, as disclosed in WO 2002/ 28414) to induce a CTL were examined using PBMCs from HLA-A*1101-positive healthy donors 1-3 according to the method as described above. Results are shown in FIGS. 10-14. In the figs, longitudinal axes represent specific lysis (%), and horizontal axes represent E/T ratios. BLCL-Ps are represented using full lines, and BLCL-NPs are represented using dotted lines. It was confirmed that $WT1_{378}$ peptide dimer has an ability to induce a CTL. Furthermore, it was found that the ability of each WT1$_{379}$ peptide of which the amino acid sequence is different from that of WT1$_{378}$ peptide by one amino acid in the amino acid sequence of WT1 protein to induce a CTL is much lower than that of WT1$_{378}$ peptide and, thus, the WT1 peptide of the present invention has an excellent and unexpected effect as compared with the known peptide.

INDUSTRIAL APPLICABILITY

The present invention provides an HLA-A*1101-restricted WT1 peptide, a polynucleotide encoding the peptide, a pharmaceutical composition comprising the same and the like. Therefore, the present invention can be used in the fields of medicine and the like, for example, in the fields of development and preparation of a pharmaceutical composition for the prevention or treatment of various hematopoietic tumors and solid cancers that express WT1 gene at high levels.

Sequence Listing Free Text

SEQ ID NO: 11: Modified WT1 peptide
SEQ ID NO: 12: Modified WT1 peptide

The invention claimed is:

1. An isolated peptide consisting of an amino acid sequence selected from:

```
                                          (SEQ ID No: 6)
Ser His Leu Gln Met His Ser Arg Lys,
and
                                          (SEQ ID No: 7)
Thr Gly Val Lys Pro Phe Gln Cys Lys.
```

2. The isolated peptide according to claim 1, wherein the amino acid sequence is Thr Gly Val Lys Pro Phe Gln Cys Lys (SEQ ID No: 7).

3. An isolated peptide dimer comprising a first and second peptide monomer bound through a disulfide bond, wherein
(1) the first peptide monomer consists of an amino acid sequence Thr Gly Val Lys Pro Phe Gln Cys Lys (SEQ ID No: 7); and
(2) the second peptide monomer consists of an amino acid sequence selected from:

```
                                          (SEQ ID No: 3)
Pro Ile Leu Cys Gly Ala Gln Tyr Arg, (SEQ ID No: 7)
Thr Gly Val Lys Pro Phe Gln Cys Lys, (SEQ ID No: 8)
Lys Thr Cys Gln Arg Lys Phe Ser Arg,
and
                                          (SEQ ID No: 9)
Ser Cys Arg Trp Pro Ser Cys Gln Lys.
```

4. A pharmaceutical composition for the induction of a Wilms' tumor gene (WT1)-specific cytotoxic T cell (CTL), comprising the isolated peptide dimer according to claim 3 as an active ingredient and a carrier or excipient.

5. A polynucleotide encoding the peptide according to claim 1.

6. An expression vector comprising the polynucleotide according to claim 5.

7. A pharmaceutical composition for the induction of a WT1-specific CTL, comprising the polynucleotide according to claim 5 or the vector according to claim 6.

8. A method for the induction of a WT1-specific CTL, comprising administering an effective amount of the polynucleotide according to claim 5 or the vector according to claim 6 to an HLA-A*1101-positive subject.

9. A kit comprising the isolated peptide dimer according to claim 3 as an essential component.

10. A pharmaceutical composition for the induction of a WT1-specific CTL, comprising an isolated peptide as an active ingredient and a carrier or excipient, wherein
the isolated peptide consists of an amino acid sequence selected from:

```
                                          (SEQ ID No: 5)
Ser Ala Ser Glu Thr Ser Glu Lys Arg, (SEQ ID No: 6)
Ser His Leu Gln Met His Ser Arg Lys,
and
                                          (SEQ ID No: 7)
Thr Gly Val Lys Pro Phe Gln Cys Lys.
```

11. A kit comprising an isolated peptide as an essential component, wherein
the isolated peptide consists of an amino acid sequence selected from:
Ser Ala Ser Glu Thr Ser Glu Lys Arg (SEQ ID No: 5),
Ser His Leu Gln Met His Ser Arg Lys (SEQ ID No: 6), and
Thr Gly Val Lys Pro Phe Gln Cys Lys (SEQ ID No: 7).

* * * * *